US010188287B2

(12) United States Patent
Copland et al.

(10) Patent No.: US 10,188,287 B2
(45) Date of Patent: Jan. 29, 2019

(54) OPTICAL MEASUREMENT SYSTEMS AND METHODS WITH CUSTOM CHROMATIC ABERRATION ADJUSTMENTS

(71) Applicant: AMO WaveFront Sciences, LLC, Santa Ana, CA (US)

(72) Inventors: Richard J. Copland, Albuquerque, NM (US); Daniel R. Neal, Tijeras, NM (US); Thomas D. Raymond, Edgewood, NM (US); Stephen W. Farrer, Albuquerque, NM (US)

(73) Assignee: AMO WaveFront Sciences, LLC, Santa Ana, CA (US)

( * ) Notice: Subject to any disclaimer, the term of this patent is extended or adjusted under 35 U.S.C. 154(b) by 70 days.

(21) Appl. No.: 15/282,338

(22) Filed: Sep. 30, 2016

(65) Prior Publication Data

US 2017/0095147 A1 Apr. 6, 2017

Related U.S. Application Data

(60) Provisional application No. 62/236,083, filed on Oct. 1, 2015.

(51) Int. Cl.
*A61B 3/14* (2006.01)
*A61B 3/103* (2006.01)
(Continued)

(52) U.S. Cl.
CPC .......... *A61B 3/103* (2013.01); *A61B 3/0025* (2013.01); *A61B 3/102* (2013.01); *A61B 3/107* (2013.01);
(Continued)

(58) Field of Classification Search
CPC ........... A61B 3/107; A61B 3/14; A61B 3/103; A61B 3/0091; A61B 3/1015; A61B 3/158
(Continued)

(56) References Cited

U.S. PATENT DOCUMENTS

| 5,777,719 A | 7/1998 | Williams et al. |
|---|---|---|
| 6,550,917 B1 | 4/2003 | Neal et al. |
| 7,980,699 B2 | 7/2011 | Neal et al. |
| 7,988,290 B2 | 8/2011 | Campbell et al. |
| 8,500,283 B1 | 8/2013 | Swinger |
| 2011/0085139 A1* | 4/2011 | Blixt ...................... A61B 3/113 351/209 |

(Continued)

OTHER PUBLICATIONS

Mejia-Barbosa Y., et al., "Object Surface for Applying a Modified Hartmann Test to Measure Corneal Topography," Applied Optics, 2001, vol. 40 (31), pp. 5778-5786.

(Continued)

*Primary Examiner* — Mahidere Sahle
(74) *Attorney, Agent, or Firm* — Johnson & Johnson Surgical Vision, Inc.

(57) ABSTRACT

An optical measurement system method for measuring a characteristic of a subject's eye use a probe beam having an infrared wavelength in the infrared spectrum to measure a refraction of the subject's eye at the infrared wavelength; capture at least two different Purkinje images at two different corresponding wavelengths from at least one surface of the lens of the subject's eye; determine from the at least two different Purkinje images a value for at least one parameter of the subject's eye; use the value of the at least one parameter to determine a customized chromatic adjustment factor for the subject's eye; and correct the measured refraction of the subject's eye at the infrared wavelength with the customized chromatic adjustment factor to determine a refraction of the subject's eye at a visible wavelength in the visible spectrum.

24 Claims, 16 Drawing Sheets

(51) Int. Cl.
    *A61B 3/00*            (2006.01)
    *A61B 3/10*            (2006.01)
    *A61B 3/107*          (2006.01)
    *A61B 3/117*          (2006.01)
    *A61B 3/18*            (2006.01)
    *A61B 5/00*            (2006.01)

(52) U.S. Cl.
    CPC .......... *A61B 3/1015* (2013.01); *A61B 3/1173* (2013.01); *A61B 3/14* (2013.01); *A61B 3/18* (2013.01); *A61B 5/0075* (2013.01); *A61B 2576/02* (2013.01)

(58) Field of Classification Search
    USPC ....................................................... 351/206
    See application file for complete search history.

(56) References Cited

U.S. PATENT DOCUMENTS

| | | |
|---|---|---|
| 2011/0202017 A1 | 8/2011 | Reimer |
| 2012/0140173 A1* | 6/2012 | Uhlhorn ................. A61B 3/102 |
| | | 351/206 |
| 2014/0268044 A1 | 9/2014 | Copland |

OTHER PUBLICATIONS

International Search Report and Written Opinion for Application No. PCT/US2016/054861, dated Jan. 25, 2017, 10 pages.

\* cited by examiner

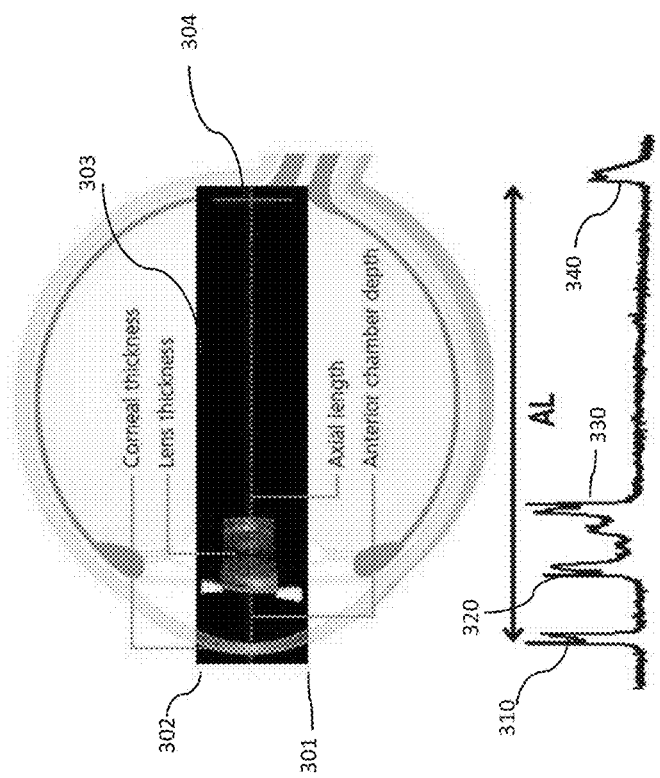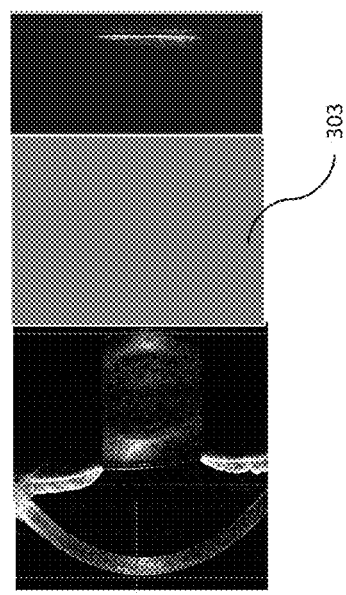
FIG. 6A  FIG. 6B  FIG. 6C

1200

1210 — Using a probe beam having an infrared wavelength in the infrared spectrum to measure a refraction of the subject's eye at the infrared wavelength 1220 — Capturing at least two different Purkinje images at two different corresponding wavelengths from at least one surface of the lens of the subject's eye 1230 — Determining from the at least two different Purkinje images a value for at least one parameter of the subject's eye 1240 — Using the value of the at least one parameter to determine a customized chromatic adjustment factor for the subject's eye 1250 — Correcting the measured refraction of the subject's eye at the infrared wavelength with the customized chromatic adjustment factor to determine a refraction of the subject's eye at a visible wavelength in the visible spectrum

FIG. 12

OPTICAL MEASUREMENT SYSTEMS AND METHODS WITH CUSTOM CHROMATIC ABERRATION ADJUSTMENTS

CROSS-REFERENCE

This application claims the benefit under 35 U.S.C. § 119(e) of U.S. Provisional Patent Application No. 62/236,083, filed Oct. 1, 2015, the full disclosures of which are incorporated herein by reference.

TECHNICAL FIELD

Embodiments of this invention pertain to optical measurement equipment, and more particularly, to optical measurement systems and processes which include components and methods for making adjustments or corrections for individual chromatic aberrations unique to each particular subject's eye.

BACKGROUND

A wide variety of optical measurement instruments are now available to characterize one of more parameters of a subject's eye. On such optical measurement instrument is an aberrometer, which may be employed to obtain objective refraction measurements of a subject's eye. An aberrometer may include a Shack-Hartmann wavefront sensor, which may measure the values for one of more refraction orders of a subject's eye from a light wavefront which is returned from the eye.

Aberrometers typically measure the refraction of a subject's eye using infrared light.

However, in general a physician or clinician wants to know the refraction of a subject's eye with visible light. So a chromatic adjustment must be made between the infrared light using for the measurements and the visible light for which the refraction is sought. In this patent application, we will refer to such an adjustment as a "Chromatic Adjustment Factor (CAF)."

Typically, an optical measurement instrument which includes as an aberrometer or autorefractor simply subtracts 0.7 diopters from the infrared refraction to get the visible refraction. That is, it applies a CAF of 0.7. A CAF of 0.7 brings the average calculated visible refraction into agreement with the average manifest refraction over a large sample of subject eyes.

However, tests indicate that for about twenty percent of subjects, the refraction for the subject in the visible spectrum which is obtained by applying a standard CAF of 0.7 to the value measured by the instrument using infrared light will be have a difference or "error" of more than 0.5 diopters from the correct value for that eye. Eye glasses prescribed with such an error will result in complaints from many subjects. It is believed that this error is a product of the fact that the correct CAF which should be applied varies from eye to eye, depending on differences between subjects in parameters such as the change in the index of refraction of the cornea from the infrared wavelength to the visible wavelength, the change in the index of refraction of the lens from the infrared wavelength to the visible wavelength, etc.

Accordingly, it would be desirable to improve the CAF value used with aberrometer measurements so that the calculated visible refraction matches better to the manifest refraction that an optometrist would determine with a phoropter.

SUMMARY

According to one or more aspects of the present invention, a method is provided for measuring a characteristic of a subject's eye which includes a cornea and a lens. The method comprises: using a probe beam having an infrared wavelength in the infrared spectrum to measure a refraction of the subject's eye at the infrared wavelength; capturing at least two different Purkinje images at two different corresponding wavelengths from at least one surface of the lens of the subject's eye; determining from the at least two different Purkinje images a value for at least one parameter of the subject's eye; using the value of the at least one parameter to determine a customized chromatic adjustment factor for the subject's eye; and correcting the measured refraction of the subject's eye at the infrared wavelength with the customized chromatic adjustment factor to determine a refraction of the subject's eye at a visible wavelength in the visible spectrum.

In some embodiments, the at least two different Purkinje images include at least two Purkinje III images from an anterior surface of the lens.

In some versions of these embodiments, the method further comprises measuring a curvature of the cornea of the subject's eye, wherein determining from at least two different Purkinje images a value for at least one parameter of the eye includes determining from the measured curvature of the cornea and the at least two Purkinje III images a change in an index of refraction of the cornea from the infrared wavelength to the visible wavelength.

In some versions of these embodiments, the at least two different Purkinje images further include at least two Purkinje IV images from a posterior surface of the lens.

In some versions of these embodiments, determining from at least two different Purkinje images a value for at least one parameter of the eye includes determining from the at least two Purkinje III images and the at least two Purkinje IV images a change in an index of refraction of the lens from the infrared wavelength to the visible wavelength.

In some versions of these embodiments, determining from the at least two different Purkinje images a value for at least one parameter of the eye includes determining from the at least two Purkinje IV images a radius of curvature of the posterior surface of a lens of the eye.

In some versions of these embodiments, the method further comprises: employing an optical coherence tomographer to measure a thickness of a lens of the eye; and using the measured thickness of the lens to determine the customized chromatic adjustment factor for the eye.

In some versions of these embodiments, determining from the at least two different Purkinje images a value for at least one parameter of the eye includes determining from the at least two Purkinje III images a radius of curvature of the anterior surface of a lens of the eye.

In some embodiments, the two wavelengths include the infrared wavelength.

In some embodiments, the two wavelengths are both in the infrared spectrum.

In some embodiments, using the value for at least one parameter to determine a customized chromatic adjustment factor for the subject's eye includes performing ray tracing using an eye model including the at least one parameter, wherein the value for the at least parameter is employed in the ray tracing.

In some embodiments, using the value for at least one parameter to determine a customized chromatic adjustment factor for the subject's eye includes solving a linear equation wherein at least one variable in the linear equation corresponds to the at least one parameter, wherein solving the linear equation includes substituting the value for the at least one variable in the linear equation According to one or more other aspects of the present invention, a system is provided for making at least one objective measurement of a subject's eye. The system includes: an aberrometer comprising a light source configured to generate a probe beam having an infrared wavelength in the infrared spectrum, the aberrometer being configured to measure a refraction of the subject's eye at the infrared wavelength; a light pattern generator configured to generate light patterns at two different wavelengths; an image detector configured to capture at least two different Purkinje images at the two different wavelengths from at least one surface of the lens of the subject's eye; and at least one processor. The at least one processor is configured to: determine from the at least two different Purkinje images a value for at least one parameter of the subject's eye, determine a customized chromatic adjustment factor for the subject's eye based at least in part on the value of the at least one parameter to, and correct the measured refraction of the subject's eye at the infrared wavelength with the customized chromatic adjustment factor to determine a refraction of the subject's eye at a visible wavelength in the visible spectrum.

In some embodiments, the at least two different Purkinje images include at least two Purkinje III images from an anterior surface of the lens.

In some versions of these embodiments, the system further comprises a corneal topographer configured to measure a curvature of the cornea of the subject's eye, wherein the processor is configured to determine from the measured curvature of the cornea and the at least two Purkinje III images a change in an index of refraction of the cornea from the infrared wavelength to the visible wavelength.

In some versions of these embodiments, the at least two different Purkinje images further include at least two Purkinje IV images from a posterior surface of the lens.

In some versions of these embodiments, the processor is configured to determine from the at least two Purkinje III images and the at least two Purkinje IV images a change in an index of refraction of the lens from the infrared wavelength to the visible wavelength.

In some versions of these embodiments, the processor is configured to determine from the at least two Purkinje IV images a radius of curvature of the posterior surface of a lens of the eye.

In some versions of these embodiments, the processor is configured to determine from the at least two Purkinje III images a radius of curvature of the anterior surface of a lens of the eye.

In some versions of these embodiments, the system further comprises an optical coherence tomographer configured to measure a thickness of a lens of the eye, wherein the processor is further configured to determine the customized chromatic adjustment factor for the subject's eye at least In part using the measured thickness of the lens.

In some embodiments, the two wavelengths include the infrared wavelength.

In some embodiments, the two wavelengths are both in the infrared spectrum.

In some embodiments, the processor is configured to perform ray tracing using an eye model including the at least one parameter, wherein the value for the at least parameter is employed in the ray tracing.

In some embodiments, the processor is configured to solve a linear equation wherein at least one variable in the linear equation corresponds to the at least one parameter, wherein solving the linear equation includes substituting the value for the at least one variable in the linear equation.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

All patents and patent applications cited here are hereby incorporated by reference hereby reference in their entirety. U.S. Patent Publication No. 2009/0161090, entitled "Systems and Methods for Measuring the Shape and Location of an Object," is hereby incorporated by reference in its entirety.

The use of the terms "a" and "an" and "the" and similar referents in the context of describing the invention (especially in the context of the following claims) are to be construed to cover both the singular and the plural, unless otherwise indicated here or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values here are merely intended to serve as a shorthand method of referring individually to each separate value falling within the range, unless otherwise indicated herein, and each separate value is incorporated into the specification as if it were individually recited herein. All methods described here can be performed in any suitable order unless otherwise indicated here or otherwise clearly contradicted by context. The use of any and all examples, or exemplary language (e.g., "such as") provided herein, is intended merely to better illuminate embodiments of the invention, and does not pose a limitation on the scope of the invention unless otherwise claimed. No language in the specification should be construed as indicating any non-claimed element as essential to the practice of the invention.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

FIG. 6A illustrates a preferred scanning region for the OCT subsystem according to many embodiments of the present invention.

FIG. 6B shows a representative graph of an intensity of an OCT signal of an OCT subsystem 190 according to many embodiments as a function of depth along the axis defining the axial length of the eye.

FIG. 6C shows a cross-section of an eye obtained by an optical measurement system of the present invention using an OCT subsystem according to the present invention

FIG. 12 is a flowchart of an example embodiment of a method for measuring a chromatically corrected refraction of a subject's eye.

DETAILED DESCRIPTION

Exemplary embodiments of optical measurement systems and methods for performing custom chromatic adjustments to refraction measurements of an eye are described below, to illustrate various aspects and advantages of these systems and methods. However, it should be understood that the principles involved in these devices and methods can be employed in a variety of other contexts, and therefore the novel devices and method disclosed and claimed here should not be construed as being limited to the example embodiments described below.

Figure 1C:
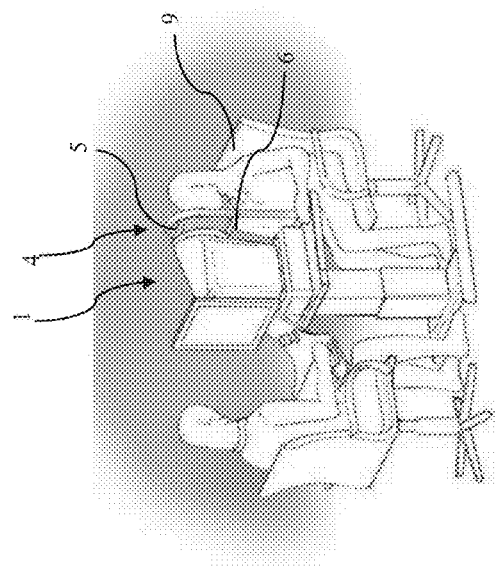
FIG. 1C illustrates a side perspective view showing an optical measurement system according to many embodiments.
Figure 1A:
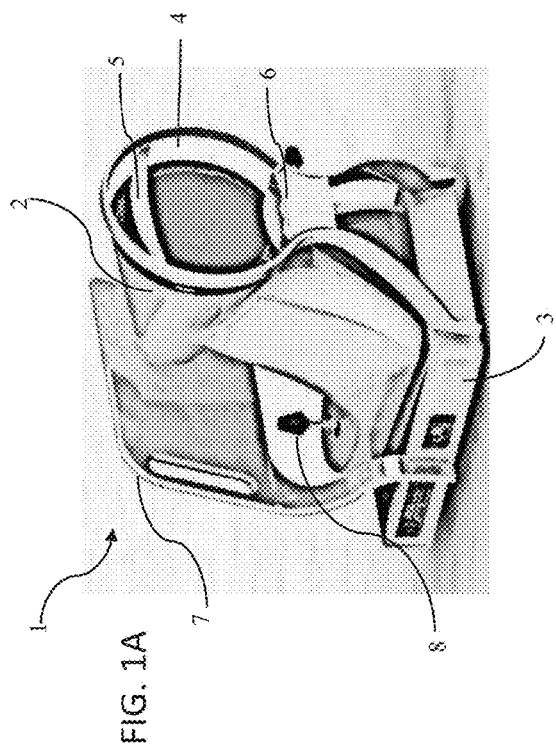
FIG. 1A illustrates a front perspective view showing an optical measurement system according to many embodiments.
Figure 1B:
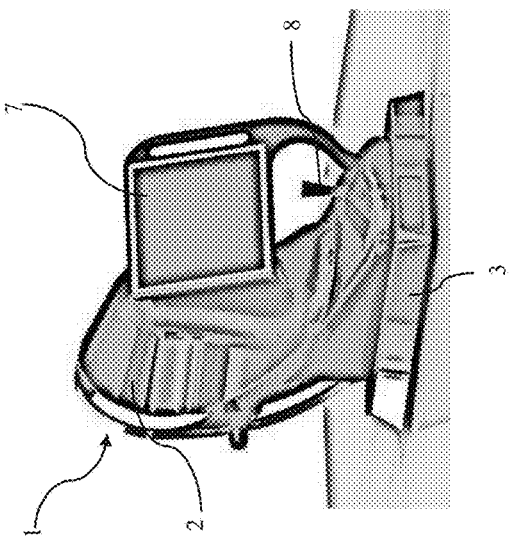
FIG. 1B illustrates a rear perspective view showing an optical measurement system according to many embodiments.

As shown in FIGS. 1A-1C, an optical measurement system 1, according to many embodiments, is operable to provide for a plurality of measurements of the human eye, including measurements of the cornea, the lens capsule, the lens and the retina. The main unit 2 comprises a base 3 and includes many primary subsystems of many embodiments of the system 1. For example, externally visible subsystems include a touch-screen display control panel 7, a patient interface assembly 4 and a joystick 8.

The patient interface 4 preferably includes one or more structures configured to hold a patient's head in a stable, immobile and preferably comfortable position during the diagnostic measurements while also maintaining the eye of the patient in a suitable alignment with the diagnostic system. In a particularly preferred embodiment, the eye of the patient remains in substantially the same position relative to the diagnostic system for all diagnostic and imaging measurements performed by the system 1.

In one embodiment the patient interface includes a chin support 32 and/or a forehead rest 4 configured to hold the head of the patient in a single, uniform position suitably aligned with respect to the system 1 throughout the diagnostic measurement. As shown in FIG. 1C, the optical measurement system 1 is preferably disposed so that the patient may be seated in a patient chair 9. The patient chair 6 can be configured to be adjusted and oriented in three axes (x, y, and z) so that the patent's head can be at a suitable height and lateral position for placement on the patient interface.

In many embodiments, the system 1 may include external communication connections. For example, the system 1 can include a network connection (e.g., an RJ45 network connection) for connecting the system 1 to a network. The network connection can be used to enable network printing of diagnostic reports, remote access to view patient diagnostic reports, and remote access to perform system diagnostics. The system 1 can include a video output port (e.g., HDMI) that can be used to output video of diagnostic measurements performed by the system 2. The output video can be displayed on an external monitor for, for example, viewing by physicians or users. The output video can also be recorded for, for example, archival purposes. The system 2 can include one or more data output ports (e.g., USB) to enable export of patient diagnostic reports to, for example, a data storage device or a computer readable medium, for example a non-volatile computer readable medium. The diagnostic reports stored on the data storage device or computer readable medium can then be accessed at a later time for any suitable purpose such as, for example, printing from an external computer in the case where the user without access to network based printing or for use during surgery, including laser cataract surgery.

Figure 2:
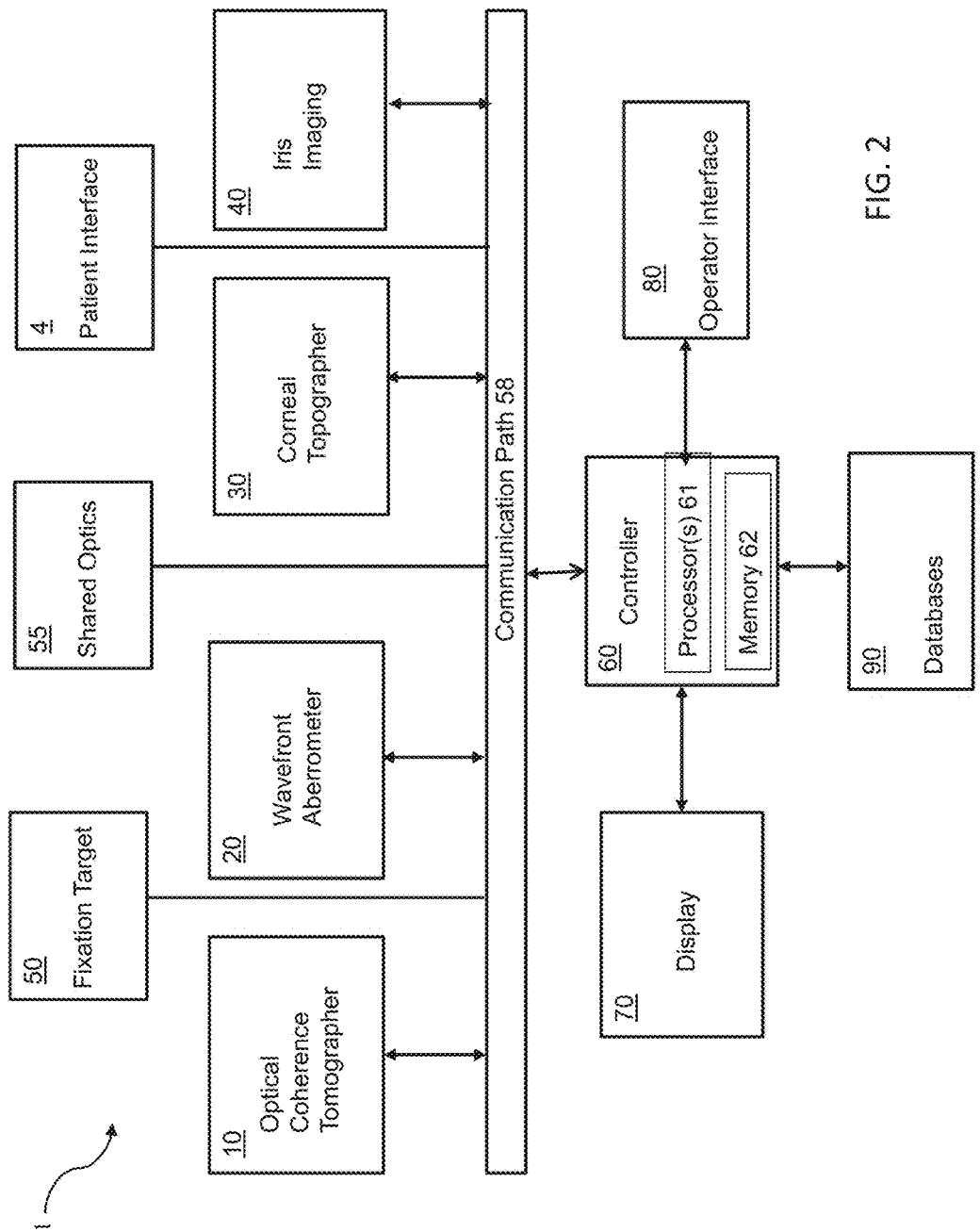
FIG. 2 is a block diagram of a system including an optical measurement instrument, and a position of an eye relative to the system according to one or more embodiments described herein which may be used by the optical measurement.

FIG. 2 is a block diagram of a system including an optical measurement instrument 1 according to one or more embodiments described herein. Optical measurement instrument 1 includes: an optical coherence tomographer (OCT) subsystem 10, a wavefront aberrometer subsystem 20, and a corneal topographer subsystem 30 for measuring one or more characteristics of a subject's eye. Optical measurement instrument 1 may further include an iris imaging subsystem 40, a fixation target subsystem 50, a controller 60, including one or more processor(s) 61 and memory 62, a display 70 and an operator interface 80. Optical measurement instrument 1 further includes a patient interface 4 for a subject to present his or her eye for measurement by optical measurement instrument 1.

The optical coherence tomography subsystem 10 is configured to measure the spatial disposition (e.g., three-dimensional coordinates such as X, Y, and Z of points on boundaries) of eye structures in three dimensions. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, the limbus and/or the retina. The spatial disposition of the structures of interest and/or of suitable matching geometric modeling such as surfaces and curves can be generated and/or used by the controller for a number of purposes, including, in some embodiment to program and control a subsequent laser-assisted surgical procedure. The spatial disposition of the structures of interest and/or of suitable matching geometric modeling can also be used to determine a wide variety of parameters. In some embodiments, the dimensions of these structures may be employed to determine a custom Chromatic Adjustment Factor (CAF) which can be applied to refraction measurements made on the eye using infrared light in order to obtain corrected values for the visible light spectrum.

As a non-limiting example, the system 1 can be configured to use a swept source OCT imaging system employing wavelengths of around 1060 nm with an 8 mm scan depth. The spatial disposition of the eye structures using optical coherence tomography should generally be measured while the patient is engaged with patient interface 4. The OCT scan depth is preferably between 8 and 50 mm, and the scan depth is preferably greater than about 24 mm or even 30 mm to achieve a full eyescan depth. The swept source wavelengths can be centered at wavelengths from 840 nm to 1310 nm.

Optical coherence tomographer subsystem 10 is only one example of an eye structure imaging subsystem which may be employed in optical measurement instrument 1. In other embodiments, a different eye structure imaging subsystem may be employed, for example a Scheimplug Imager, a fluorescence imager, a structured lighting imager, a wavefront tomographer, an ultrasound imager and a plenoptic imager.

Wavefront aberrometer subsystem 20 is configured to measure ocular aberrations, preferably including low and high order aberrations, by measuring the wavefront emerging from the eye by, for example a Shack-Hartmann wavefront sensor.

The corneal topographer subsystem 30 may apply any number of modalities to measure the shape of the cornea including one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Shack-Hartmann measurement of the eye, a Scheimpflug image topography of the eye, a confocal tomography of the eye, a Helmholtz source topographer, or a low coherence reflectometry of the eye. The shape of the cornea should generally be measured while the patient is engaged with patient interface 4.

Fixation target system 50 is configured to control the patient's accommodation, because it is often desired to measure the refraction and wavefront aberrations when eye 101 is focused at its far point Images captured by the corneal topographer subsystem 10, the wavefront aberrometer 20, the optical coherence tomographer subsystem 30 or the camera 40 may be displayed with a display of the operator interface 80 of the optical measurement system 2 or the display 70 of the optical measurement system, respectively. The operator interface may also be used to modify, distort, or transform any of the displayed images.

The shared optics 55 provide a common propagation path that is disposed between the patient interface 4 and each of the optical coherence tomographer (OCT) subsystem 10, the wavefront aberrometer subsystem 20, the corneal topographer subsystem 30, and in some embodiments, the camera 40, and the fixation target 50. In many embodiments, the shared optics 55 may comprise a number of optical elements, including mirrors, lenses and beam combiners to receive the emission from the respective subsystem to the patient's eye and, in some cases, to redirect the emission from a patient's eye along the common propagation path to an appropriate director.

The controller 60 controls the operation of the optical measurement instrument 1 and can receive input from any of the optical coherence tomographer (OCT) subsystem 10, the wavefront aberrometer subsystem 20, the corneal topographer subsystem 30 for measuring one or more characteristics of a subject's eye, the camera 40, the fixation target 50, the display 70 and the operator interface 80 via the communication paths 58. The controller 60 can include any suitable components, such as one or more processor, one or more field-programmable gate array (FPGA), and one or more memory storage devices. In many embodiments, the controller 60 controls the display 70 to provide for user control over a laser eye surgery procedure according to user specified treatment parameters as well as to provide user control over the laser eye surgery procedure. The communication paths 58 can be implemented in any suitable configuration, including any suitable shared or dedicated communication paths between the controller 60 and the respective system components.

The operator interface 80 can include any suitable user input device suitable to provide user input to the controller 60. For example, the user interface devices 80 can include devices such as joystick 8, a keyboard or a touchscreen display 70.

Figure 3A:
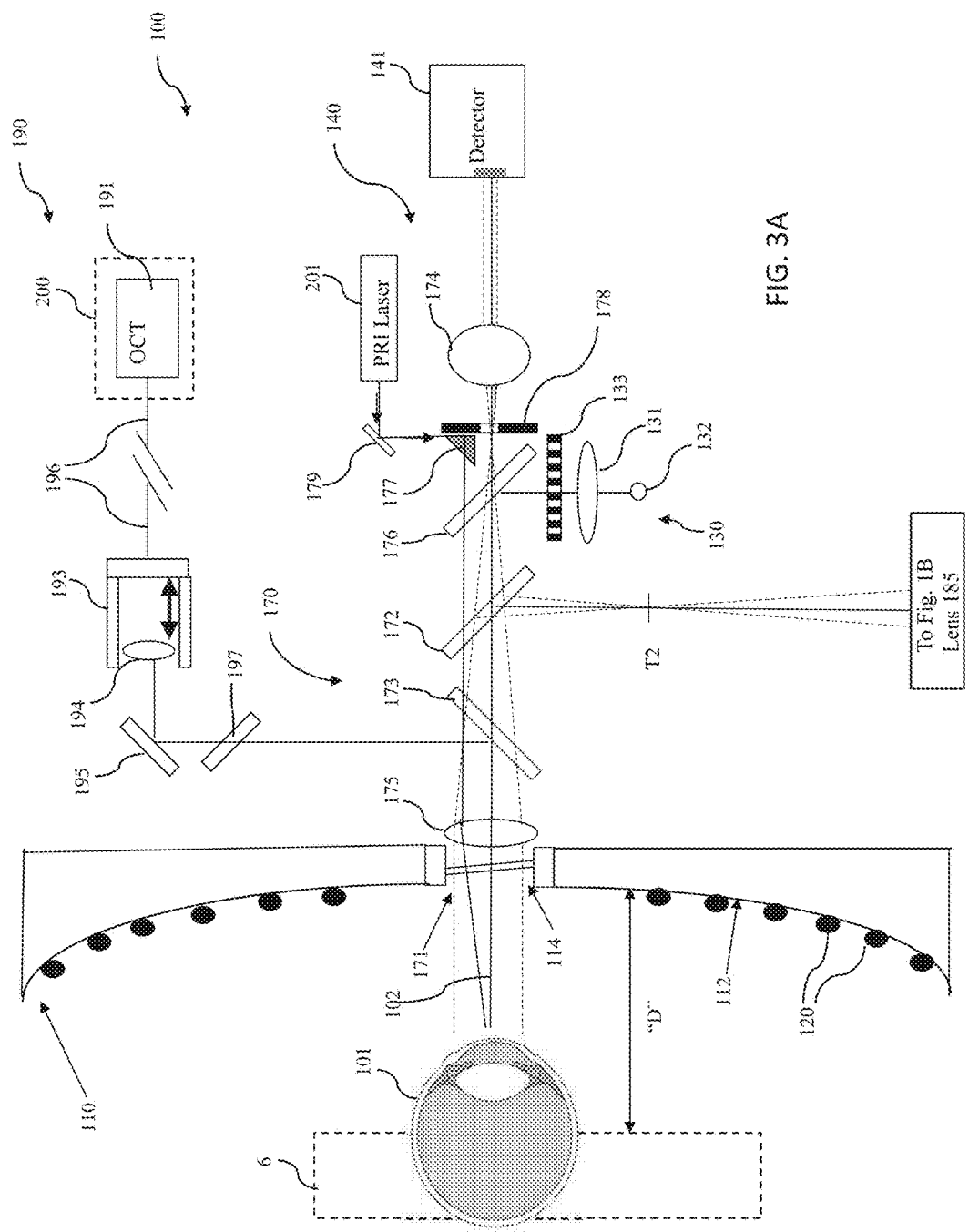
FIGS. 3A and 3B illustrate together an assembly illustrating a suitable configuration and integration of an optical coherence tomographer subsystem, a wavefront aberrometer subsystem a corneal topographer subsystem, an iris imaging subsystem, a fixation target subsystem according to a non-limiting embodiment of the present invention.
Figure 3B:
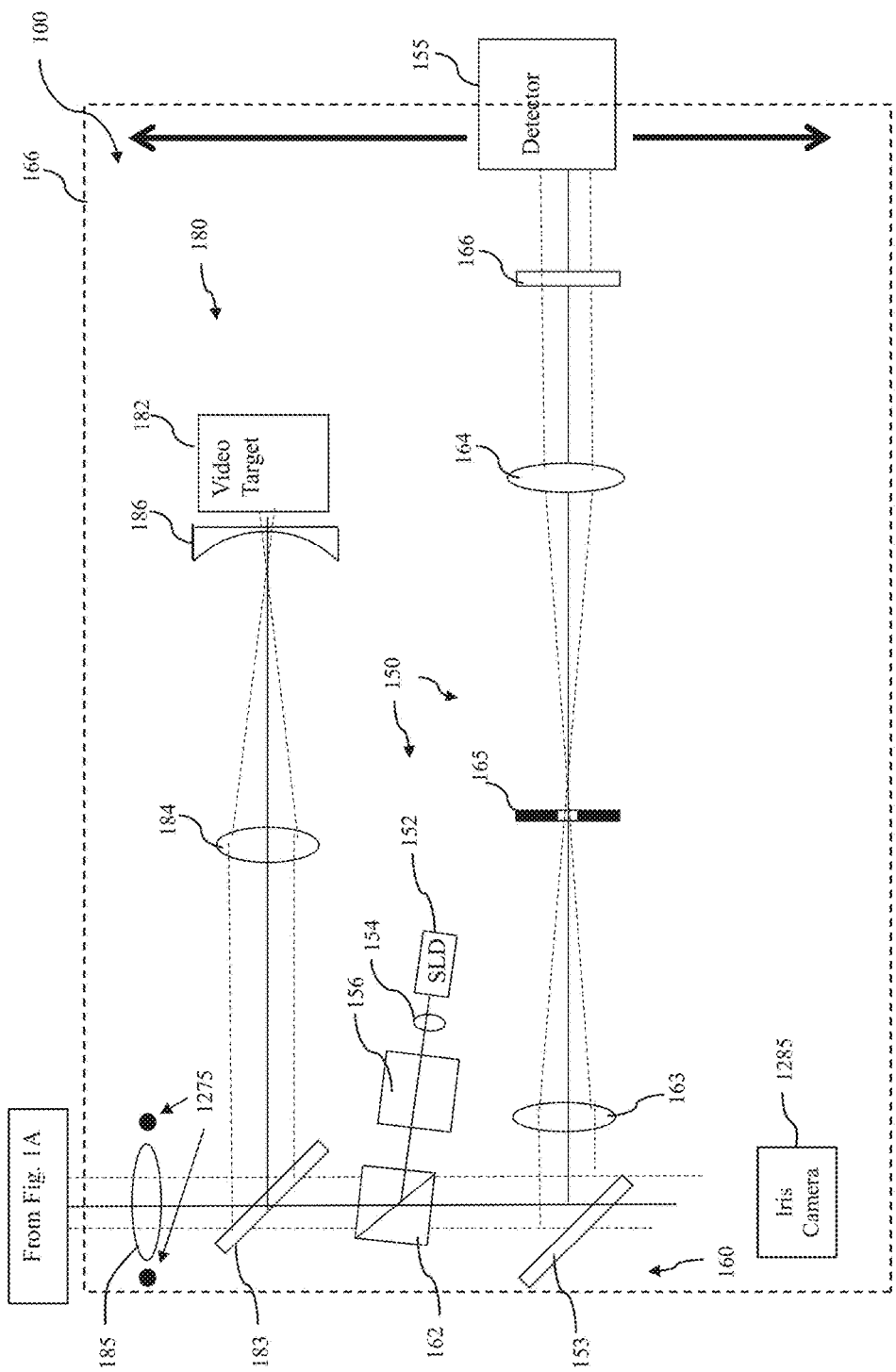

FIGS. 3A and 3B are simplified block diagrams illustrating an assembly 100 according to many embodiments, which can be included in the system 1. The assembly 100 is a non-limiting example of suitable configurations and integration of the optical coherence tomographer (OCT) subsystem 190, the wavefront aberrometer subsystem 150, the corneal topographer subsystem 140 for measuring one or more characteristics of a subject's eye, a camera 40, the fixation target subsystem 180 and the shared optics.

The shared optics generally comprise one or more components of a first optical system 170 disposed along a central axis 102 passing through the opening or aperture 114 of the structure 110. A first optical system 170 directs light from the various light sources along the central axis 102 towards the eye and establishes a shared or common optical path along which the light from the various light sources travel to the eye 101. In one embodiment, optical system 170 comprises a quarter wave plate 171, a first beamsplitter 172, a second beamsplitter 173, an optical element (e.g., a lens) 174, a second lens 175, a third beamsplitter 176, and a structure including an aperture 178. Additional optical systems may be used in assembly 100 to direct light beams from one or more light sources to the first optical system 170. For example, a second optical system 160 directs light to the first optical system 170 from the wavefront aberrometer subsystem 150 and comprises mirror 153, beam splitter 162 and beam splitter 183 and lens 185.

Other configurations of the assembly 100 may be possible and may be apparent to a person of skill in the art.

The corneal topographer subsystem 140 comprises a structure 110 having a principal surface 112 with an opening or aperture 114 therein; a plurality of first (or peripheral) light sources 120 provided on the principal surface 112 of the structure 110; a Helmholz light source 130; and a detector, photodetector, or detector array 141.

In one embodiment, structure 110 has the shape of an elongated oval or "zeppelin" with openings or apertures at either end thereof. An example of such a structure is disclosed in Yobani Meji'a-Barbosa et al., "Object surface for applying a modified Hartmann test to measure corneal topography," APPLIED OPTICS, Vol. 40, No. 31 (Nov. 1, 2001) ("Meji'a-Barbosa"). In some embodiments, principal surface 112 of structure 110 is concave when viewed from the cornea of eye 100, as illustrated in FIG. 1A.

In one embodiment where principal surface 112 is concave, principal surface 112 has the shape of a conical frustum. Alternatively, principal surface 112 may have a shape of hemisphere or some other portion of a sphere, with an opening or aperture therein. Also alternatively, principal surface 112 may have the shape of a modified sphere or conical frustum, with a side portion removed. Beneficially, such an arrangement may improve the ergonomics of assembly 100 by more easily allowing structure 110 to be more closely located to a subject's eye 100 without being obstructed by the subject's nose. Of course, a variety of other configurations and shapes for principal surface 112 are possible.

In the embodiment of FIG. 1A, the plurality of first light sources 120 are provided on the principal surface 112 of structure 110 so as to illuminate the cornea of eye 101. In one embodiment, light sources 122 may comprise individual light generating elements or lamps, such as light emitting diodes (LEDs) and/or the tips of the individual optical fibers of a fiber bundle. Alternatively, principal surface 112 of structure 110 may have a plurality of holes or apertures therein, and one or more backlight lamps, which may include reflectors and/or diffusers, may be provided for passing lighting through the holes to form the plurality of first light sources 120 which project light onto the cornea of eye 100. Other arrangements are possible.

In another embodiment, structure 110 is omitted from assembly 100, and the first light sources 120 may be independently suspended (e.g., as separate optical fibers) to form a group of first light sources 120 arranged around a central axis, the group being separated from the axis by a radial distance defining an aperture in the group (corresponding generally to the aperture 114 in the structure 110 illustrated in FIG. 1A).

In operation, a ray (solid line) from one of the first light sources 120 is reflected by the cornea and passes through optical system 170 (including aperture 178) to appear as a light spot on detector array 141. It will be appreciated that this ray is representative of a small bundle of rays that make it through optical system 170 and onto detector array 141, all of which will focus to substantially the same location on detector array 141. Other rays from that first light source 120 are either blocked by the aperture 178 or are otherwise scattered so as to not pass through the optical system 170. In similar fashion, light from the other first light sources 120 are imaged onto detector array 141 such that each one of first light sources 120 is imaged or mapped to a location on detector array 141 that may be correlated to a particular reflection location on the cornea of eye 100 and/or the shape of the cornea. Thus, detector array 141 detects the light spots projected thereon and provides corresponding output signals to a processor of controller 60 (FIG. 2). The processor determines the locations and/or shape of the light spots on detector array 141, and compares these locations and/or shapes to those expected for a standard or model cornea, thereby allowing the processor of controller 60 to determine the corneal topography. Alternatively, other ways of processing the spot images on detector array 141 may be used to determine the corneal topography of eye 101, or other information related to the characterization of eye 101.

Detector array 141 comprises a plurality of light detecting elements arranged in a two dimensional array. In one embodiment, detector array 141 comprises such a charge-coupled device (CCD), such as may be found in a video camera. However, other arrangements such as a CMOS array, or another electronic photosensitive device, may be employed instead. Beneficially, the video output signal(s) of detector array 141 are provided to processor 61 which processes these output signals as described in greater detail below.

Assembly 100 also comprises a Helmholtz light source 130 configured according to the Helmholtz principle. As used herein, the term "Helmholtz source" or "Helmholtz light source" means one or a plurality of individual light sources disposed such that light from each of the individual light sources passes through an optical element having optical power, reflects off of a reference or test object, passes through the optical element, and is received by a detector, wherein light from the Helmholtz source is used to determine geometric and/or optical information of at least a portion of a surface of the reference or test object. In general, it is a characteristic of Helmholtz sources that the signal at the detector is independent of the relative position of the test or reference object relative to the Helmholtz source. As used herein, the term "optical element" means an element that refracts, reflects, and/or diffracts light and has either positive or negative optical power.

In such embodiments, the Helmholtz light source 130 is located at optical infinity with respect to eye 100. The Helmholtz principle includes the use of such infinite sources in combination with a telecentric detector system: i.e., a system that places the detector array at optical infinity with respect to the surface under measurement, in addition to insuring that the principal measured ray leaving the surface is parallel to the optical axis of the instrument. The Helmholtz corneal measurement principle has the Helmholtz light source at optical infinity and the telecentric observing system so that detector array 141 is also optically at an infinite distance from the images of the sources formed by the cornea. Such a measurement system is insensitive to axial misalignment of the corneal surface with respect to the instrument.

In one embodiment, the Helmholtz light source 130 comprises a second light source 132 which may comprise a plurality of lamps, such as LEDs or optical fiber tips. In one embodiment, second light source 132 comprises an LED and a plate 133 with plurality of holes or apertures in a surface that are illuminated by one or more backlight lamps with an optical element 131, which may comprise diffusers.

In one embodiment, second light sources 132 are located off the central optical axis 102 of assembly 100, and light from second light sources 132 is directed toward optical element 171 by third beamsplitter 176.

The operation of the topographer portion of system 100 may be conducted with the combined use of first light source 120 and the Helmholz light source 130. In operation, detector array 141 detects the light spots projected thereon from both Helmholz light source 130 (detected at a central portion of detector array 141) and first light sources 120 (detected at a peripheral portion of detector array 141) and provides corresponding output signals to processor. In general, the images of first light sources 120 that appear on detector array 140 emanate from an outer region of the surface of the cornea, and the images of Helmholz light source 130 that appear on detector array 141 emanate from a central or paraxial region of the surface of the cornea. Accordingly, even though information about the central region of the corneal surface (e.g., surface curvature) cannot be determined from the images of first light sources 120 on detector array 141, such information can be determined from the images of Helmholz light source 130 on detector array 141. A processor of controller 60 determines the locations and/or shapes of the light spots on detector array 141, and compares these locations and/or shapes to those expected based for a standard or model cornea, thereby allowing the processor to determine the corneal topography of eye 101. Accordingly, the topography of the entire corneal surface can be characterized by system 100 without a "hole" or missing data from the central corneal region.

A fourth light source 201 off the central axis 102 may be directed along optical axis 102 by mirrors 177, 179 disposed on or near the aperture 178, perpendicular to the optical axis 102 are configured as a pupil retroreflection illuminator. The pupil retroreflection illuminator is configured to direct a disc of light toward a patient's eye, whereby the disc of light may be reflected from reflective surfaces within the eye, and the reflected light is transmitted by optical path 170 to detector 141. The pupil retroreflection illuminators may optionally be configured such that, when a patient's pupil is dilated, the disc of light from light source 201 is reflected from an implanted IOL to image the IOL, including any fiducial marks; if IOL is imperfectly placed, detector 141 may be used to determine IOL edges are decentered. Also, images from detector 141 using the pupil retroreflection illuminator may see folds, for instance, unfolded edge if the IOL did not unfold properly.

The wavefront aberrometer subsystem 150 of the assembly 100 comprises a third light source 152 providing a probe beam and a wavefront sensor 155. The Wavefront aberrometer subsystem 150 preferably further comprises a collimating lens 154, a polarizing beamsplitter 156, an adjustable telescope comprising a first optical element, lens 163 and a second optical element, lens 164, a movable stage or platform 166, and a dynamic-range limiting aperture 165 for limiting a dynamic range of light provided to wavefront sensor 155 so as to preclude data ambiguity. Light from the wavefront aberrometer subsystem is directed to one of the constituent optical elements of the optical system 170 disposed along a central axis 102 passing through the opening or aperture 114 of the structure 110. It will be appreciated by those of skill in the art that the lenses 163, 164, or any of the other lenses discussed herein, may be replaced or supplemented by another type of converging or diverging optical element, such as a diffractive optical element.

Light source 152 is preferably an 840 nm SLD (super luminescent laser diode). An SLD is similar to a laser in that the light originates from a very small emitter area. However, unlike a laser, the spectral width of the SLD is very broad, about 40 nm. This tends to reduce speckle effects and improve the images that are used for wavefront measurements.

Preferably, wavefront sensor 155 is a Shack-Hartmann wavefront sensor comprising a detector array and a plurality of lenslets for focusing received light onto its detector array. In that case, the detector array may be a CCD, a CMOS array, or another electronic photosensitive device. However, other wavefront sensors may be employed instead. Embodiments of wavefront sensors which may be employed in one or more systems described herein are described in U.S. Pat. No. 6,550,917, issued to Neal et al. on Apr. 22, 2003, and U.S. Pat. No. 5,777,719, issued to Williams et al. on Jul. 7, 1998, both of which patents are hereby incorporated herein by reference in their entirety.

The aperture or opening in the middle of the group of first light sources 120 (e.g., aperture 114 in principal surface 112 of structure 110) allows system 100 to provide a probe beam into eye 101 to characterize its total ocular aberrations. Accordingly, third light source 152 supplies a probe beam through a light source polarizing beam splitter 156 and polarizing beam splitter 162 to first beamsplitter 172 of optical system 170. First beamsplitter 172 directs the probe beam through aperture 114 to eye 101. Preferably, light from the probe beam is scattered from the retina of eye 100, and at least a portion of the scattered light passes back through aperture 114 to first beamsplitter 172. First beamsplitter 172 directs the back scattered light back through beam splitter 172 to polarizing beamsplitter 162, mirror 153 to wavefront sensor 155.

Wavefront sensor 155 outputs signals to a processor of controller 60 which uses the signals to determine ocular aberrations of eye 101. Preferably, processor 61 is able to better characterize eye 101 by considering the corneal topography of eye 101 measured by the corneal topography subsystem, which may also be determined by processor 61 based on outputs of detector array 141, as explained above.

In operation of the wavefront aberrometer subsystem 150, light from light source 152 is collimated by lens 154. The light passes through light source polarizing beam splitter 156. The light entering light source polarizing beam splitter 156 is partially polarized. Light source polarizing beam splitter 156 reflects light having a first, S, polarization, and transmits light having a second, P, polarization so the exiting light is 100% linearly polarized. In this case, S and P refer to polarization directions relative to the hypotenuse in light source polarizing beam splitter 156.

Light from light source polarizing beam splitter 156 enters polarizing beamsplitter 162. The hypotenuse of polarizing beamsplitter 162 is rotated 90 degrees relative to the hypotenuse of light source polarizing beamsplitter 156 so the light is now S polarized relative the hypotenuse of polarizing beamsplitter 162 and therefore the light reflects upwards. The light from polarizing beamsplitter 162 travels upward and passes through toward beam splitter 172, retaining its S polarization, and then travels through quarter wave plate 171. Quarter wave plate 171 converts the light to circular polarization. The light then travels through aperture 114 in principal surface 112 of structure 110 to eye 101. Preferably, the beam diameter on the cornea is between 1 and 2 mm. Then the light travels through the cornea and focuses onto the retina of eye 100.

The focused spot of light becomes a light source that is used to characterize eye 100 with wavefront sensor 155. Light from the probe beam that impinges on the retina of eye 101 scatters in various directions. Some of the light reflects back as a semi-collimated beam back towards assembly 100.

Upon scattering, about 90% of the light retains its polarization. So the light traveling back towards assembly is substantially still circularly polarized. The light then travels through aperture 114 in principal surface 112 of structure 110, through quarterwave plate 171, and is converted back to linear polarization. Quarterwave plate 171 converts the polarization of the light from the eye's retina so that it is P polarized, in contrast to probe beam received from third light source 150 having the S polarization. This P polarized light then reflects off of first beamsplitter 172, and then reaches polarizing beamsplitter 162. Since the light is now P polarized relative the hypotenuse of polarizing beamsplitter 162, the beam is transmitted and then continues onto mirror 153. After being reflected by mirror 153, light is sent to an adjustable telescope comprising a first optical element 164 and a second optical element (e.g., lens) 163 and a movable stage or platform 166. The beam is also directed through a dynamic-range limiting aperture 165 for limiting a dynamic range of light provided to wavefront sensor 155 so as to preclude data ambiguity.

When wavefront sensor 155 is a Shack-Hartmann wavefront sensor, the light is collected by the lenslet array in wavefront sensor 155 and an image of spots appears on the detector array (e.g., CCD) in wavefront sensor 155. This image is then provided to a process of the controller 60 and analyzed to compute the refraction and aberrations of eye 101.

An OCT subsystem 190 of assembly 100 preferably comprises an OCT assembly 191, and a third optical path 192 which directs the OCT beam of the OCT light source to the first optical path 170. The third optical path 192 preferably comprises a fiber optic line 196, for conducting the OCT beam from the OCT light source, a z-scan device 193 operable to alter the focus of the beam in the z-direction (i.e., along the direction of propagation of the OCT beam) under control of the controller, and x-scan device 195, and a y-scan device 197 operable to translate the OCT beam in the x and y directions (i.e., perpendicular to the direction of propagation of the of the OCT beam), respectively, under control of the controller. The OCT light source and reference arm may be incorporated into the main unit 4 of the optical measurement instrument 1 shown in FIG. 1A. Alternatively, the OCT assembly 191 may be housed in a second unit 200 and the OCT beam from the OCT source may be directed from the second housing 200 to the main unit by optical pathway 192.

The OCT systems and methods of the present invention are preferably FD-OCT (Fourier domain optical coherence tomography) systems, including either an SD-OCT (spectral domain optical coherence tomography) system or, more preferably, an SS-OCT (swept source optical coherence tomography) system. In conventional FD-OCT systems, the interference signal is distributed and integrated over numerous spectral wavelength intervals, and is inverse Fourier transformed to obtain the depth-dependent reflectivity profile of the sample. The profile of scattering as a function of depth is referred to as an A-scan (Axial-scan). The beam can be scanned laterally to produce a set of A-scans that can be combined together to form a tomogram of the sample (a B-scan).

In an SD-OCT system, various spectral wavelength intervals of the combined returned light from the reference and sample arms are spatially encoded using, for instance, a collimator, diffraction grating, and a linear detector array. Resampling of the data obtained from the linear detector array is performed in order to correct for the nonlinear spatial mapping of wavenumbers. After resampling and subtraction of the dc background, the depth profile structural information is obtained by performing the inverse Fourier transform operation. In swept-source OCT, the broad bandwidth optical source is replaced by a rapid-scanning laser source. By rapidly sweeping the source wavelength over a broad wavelength range, and collecting all the scattering information at each wavelength and at each position, the composition of the collected signal is equivalent to the spectral-domain OCT technique. The collected spectral data is then inverse Fourier transformed to recover the spatial depth-dependent information.

FD-OCT suffers from an inherent sample-independent limited depth range, typically between 1 and 5 mm. One limitation flows from the fact that FD-OCT extracts depth information from the inverse Fourier transform of a spectral interferogram. Since the spectral interferogram can only be recorded as a real signal, its Fourier transform is necessarily Hermitian symmetric about the zero path length difference (ZPD) position. As a result, the positive and negative displacements about the ZPD cannot be unambiguously resolved, which gives rise to mirror image artifacts and generally halves the useable range. This is referred to as the complex conjugate ambiguity. Another limitation is a sensitivity fall-off which results in reduced sensitivity with increasing depth. Moreover, since the signal in OCT is derived only from backscattered photons, optical attenuation from absorption and scattering generally result in a useable imaging depth of about 1-4 mm.

Figure 4:
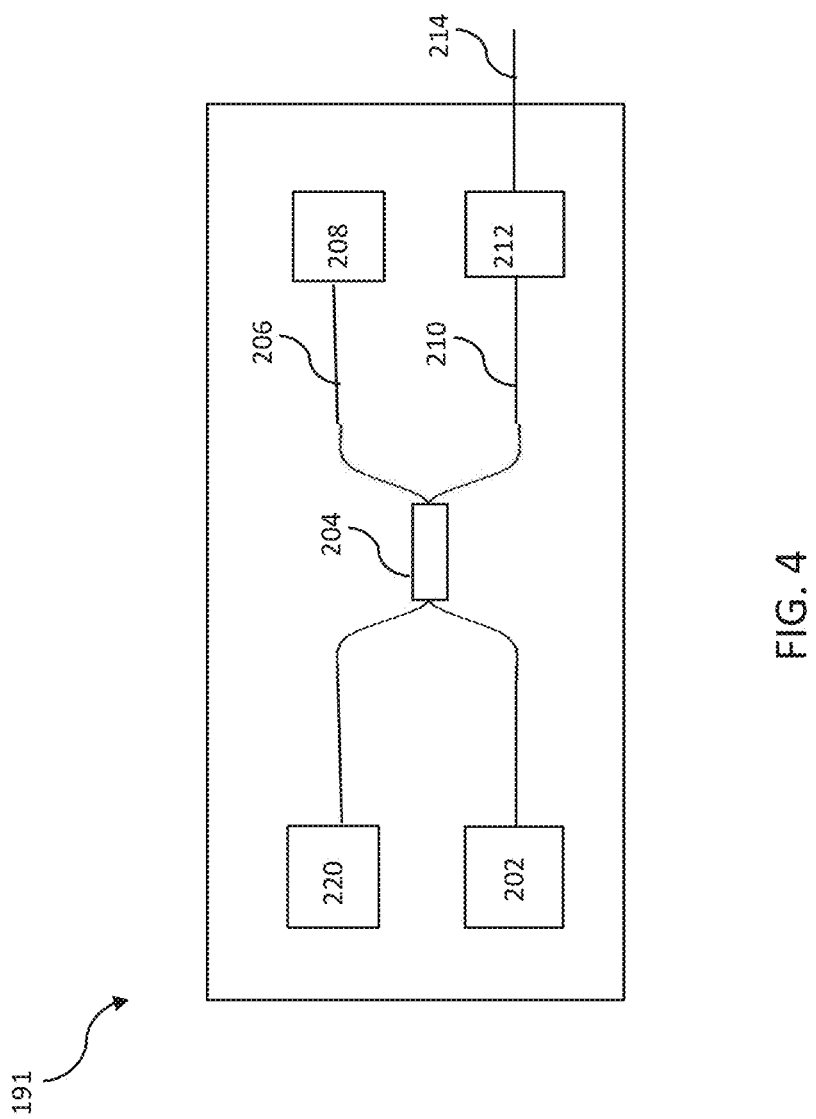
FIG. 4 is a block diagram of an OCT assembly according to many embodiments of the present invention.

Several "full range" OCT techniques have been developed that eliminate the complex conjugate artifacts to effectively double the measurement range around the ZPD position. These full range OCT techniques result in useable imaging depths of up to about 5 mm up to about 8 mm. Suitable full range techniques are methods utilizing a dithering reference lag to break the phase ambiguity, methods that use phase distortion, and other suitable methods. As shown in FIG. 4, the OCT assembly 191 of OCT subsystem 190 includes a broadband or a swept light source 202 that is split by a coupler 204 into a reference arm 206 and a sample arm 210. The reference arm 106 includes a module 108 containing a reference reflection along with suitable dispersion and path length compensation. The sample arm 110 of the OCT assembly 191 has an output connector 212 that serves as an interface to the rest of the optical measurement instrument. The return signals from both the reference and sample arms 206, 210 are then directed by coupler 204 to a detection device 220, which employs either time domain, frequency or single point detection techniques. In FIG. 4, a swept source technique is used with a laser wavelength of 1060 nm swept over a range of 8-50 mm depth.

Figure 5:
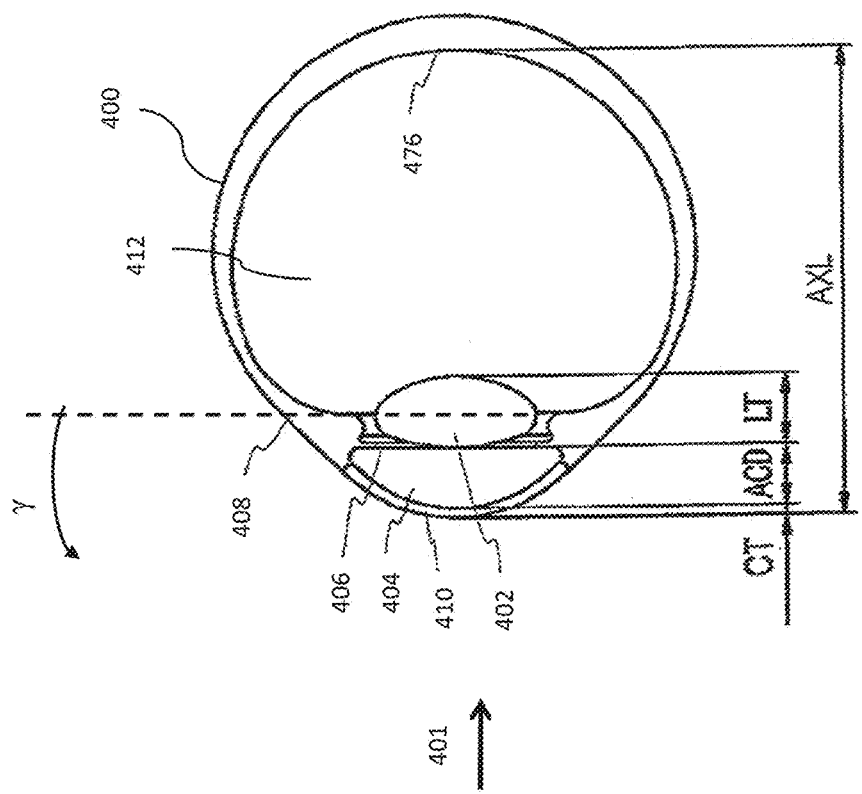
FIG. 5 is a schematic drawing of a human eye.

FIG. 5 is a schematic drawing of a human eye 400. In many embodiments, a light beam 401 from a light source enters the eye from the left of FIG. 5, refracts into the cornea 410, passes through the anterior chamber 404, the iris 406 through the pupil, and reaches lens 402. After refracting into the lens, light passes through the vitreous chamber 412, and strikes the retina 476, which detects the light and converts it to an electric signal transmitted through the optic nerve to the brain (not shown). The vitreous chamber 412 contains the vitreous humor, a clear liquid disposed between the lens 402 and retina 476. As indicated in FIG. 5, cornea 410 has corneal thickness (CT), here considered as the distance between the anterior and posterior surfaces of the cornea. Anterior chamber 404 has anterior chamber depth (ACD), which is the distance between the anterior surface of the cornea and the anterior surface of the lens. Lens 402 has lens thickness (LT) which is the distance between the anterior and posterior surfaces of the lens. The eye has an axial length (AXL) which is the distance between the anterior surface of the cornea and the retina 476. FIG. 5 also illustrates that, in many subjects the lens, including the lens capsule, may be tilted at one or more angles relative to the optical axis, including an angle γ relative to the optical axis of the eye.

The optical system may also be arranged so that the movement pattern of the scan mirrors provides a lateral motion across the retina so that the shape of the retina may be determined. It is of particular interested to measure the shape and location of the depressed region of the retina named the foveal pit. When the patient is looking directly into the instrument, with their line of sight aligned to the fixation target, the foveal pit will be in center of the OCT lateral scan. This information is beneficial in that it informs the instrument operator if the patient was looking directly at the target when the measurement was made. Retinal scans are also useful in detecting disease conditions. In some cases there may be an absence of a foveal pit that also is considered an indication of a corneal abnormality.

The average axial length of the adult human eye is about 24 mm. Since the full range imaging depth of the OCT measurements are only about 5 mm to 8 mm, then OCT scanning of the present invention preferably provides for OCT scans at different depths of the eye that can be combined together to form a combined OCT image of the eye. The OCT measurements of the present invention preferably includes OCT imaging at various depths of the patient's eye for imaging 1) at least a portion of the retina, 2) at least a portion of the anterior portion of the eye, including at least a portion of the cornea (anterior and posterior), iris, and lens (anterior and posterior), and 3) performing axial eye length measurements.

FIGS. 6A-6C illustrate various aspects of the OCT subsystem 190 according to various aspects of the present invention. FIG. 6A illustrates a preferred scanning region for the OCT subsystem according to many embodiments of the present invention. The scanning region may be defined from starting point 301 to ending point 302 at the anterior portion of the eye extending in a direction transverse the direction of propagation of the OCT beam and also extending in a direction parallel to an axis defining the axial length of the eye to the posterior portion 304 of the eye. The lateral scanning region should generally be sufficiently large in the lateral direction to permit imaging of the central portion of the cornea, at least a portion of the iris, at least a portion of the lens and at least of the retina. It should be noted that a region 303 between the posterior portion of the lens and the surface of the retina may optionally not be scanned by OCT subsystem 190 because the portion 330 does not contain anatomical structure for 3D analysis.

FIG. 6B shows a representative graph of an intensity of an OCT signal of an OCT subsystem 190 according to many embodiments as a function of depth along the axis defining the axial length of the eye. The graph generally exhibits approximately four peaks having a complex structure: (1) a peak 310 having a doublet-like structure and generally corresponding to a location of the cornea; (2) a peak 320 having a doublet-like structure and generally corresponding to a location of an anterior surface of the lens; (3) a peak 330 having a complex structure generally corresponding to a location of a posterior surface of the lens; and (4) a peak 340 generally corresponding to a location of a retina. A distance between peak 310 and peak 340 can be used to calculate the axial length (AL) of the eye. Preferably, an OCT scan by OCT subsystem 190, including both an A-scan and B-scan, is conducted at least one location in the anterior portion of the eye (e.g., a location of a cornea, a location of an anterior surface of a lens and/or a location of a posterior surface of the lens) and at least one location in the posterior portion of the eye (e.g., at a location of a retina). In some embodiments, an OCT scan by the OCT subsystem 190, including both an A-Scan and a B-scan is performed at a location corresponding to each of a location of the cornea, a location of an anterior surface of the lens, a location of a posterior surface of the lens, and a location corresponding to a retina.

It should be noted that because the OCT subsystem 190 provides for the detection of various structures of the eye, including a location of the cornea, the OCT subsystem 190 may be used as a ranging system to precisely align the patient in relation to the optical measurement system 1 of the present invention. The use of the OCT as a ranging system can significantly improve accuracy of corneal topography measurements, including keratometry measurements, which are sensitive to misalignment of the corneal structures.

FIG. 6C shows a cross-section of an eye obtained by an optical measurement system of the present invention using an OCT subsystem according to the present invention.

Figure 7:
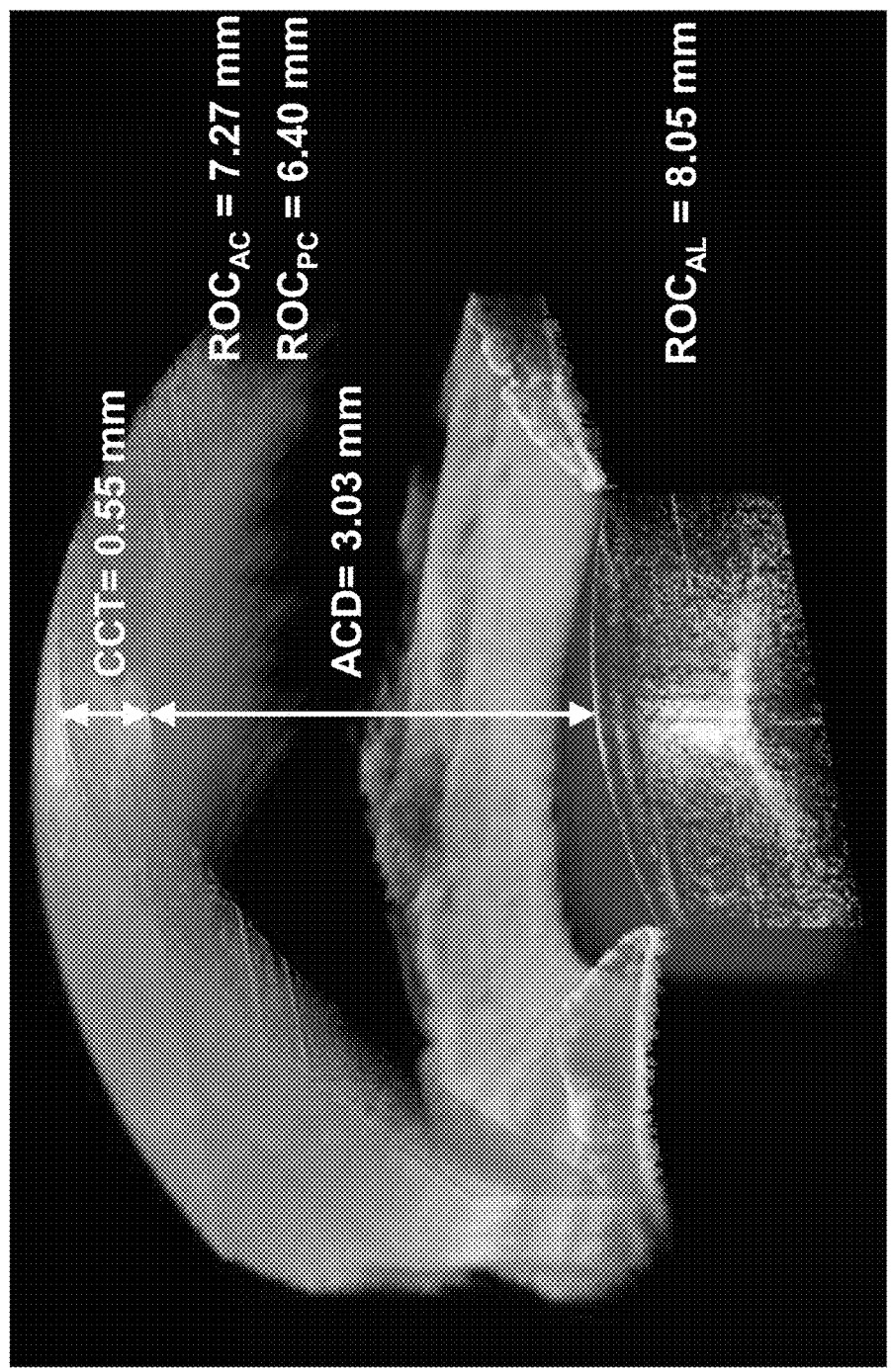
FIG. 7 is a 3-dimensional representation of an anterior portion of an eye obtained using the optical measurement system according to many embodiments.

FIG. 7 shows a 3 dimensional view of an eye obtained by an optical measurement system of the present invention using an OCT subsystem according to the present invention. FIG. 7 evidences that the OCT subsystem of the present invention is operable to obtain biometry measurements according to the present invention, including the central corneal thickness (CCT), the anterior chamber depth (ACD), the radius of curvature of the anterior cornea ($ROC_{AC}$), the radius of curvature of the Posterior cornea ($ROC_{PC}$) and the Radius of curvature of the axial length ($ROC_{AL}$).

Preferably, the OCT subsystem 190 provides sufficiently resolved structural information to provide a structural assessment that may provide a user with an indication of suitability of a particular patient for a laser cataract procedure, for example. In one embodiment, an OCT scan performed by the OCT subsystem 190 at or near the retina (i.e., a retina scan) is sufficiently resolved to identify the foveal pit location and depth, wherein a lack of depression indicates an unhealthy retina.

In another embodiment, the optical measurement instrument 1 of the present invention provides one or more measurements sufficient to provide an assessment of the tear film of a patient. In one embodiment, the tear film assessment comprises a comparison of a wavefront aberrometry map and a corneal topography map or OCT map of the patient's eye, by, for instance, subtracting the corneal topography map from the wavefront aberrometry map, to obtain a difference map. A determination of whether the tear film is broken (if not smooth); an assessment of the tear film, including tear film breakup, can be obtained by reviewing the shape of spots on the topographer. For instance, a finding or indication that the tear film is disrupted, or broken, may be based upon the shape of a spot in that, if the spots are not round, and have, for instance, an oblong or broken up shape, it indicates that tear film is disrupted. The existence of such a disrupted tear film may indicate that K value, and other ocular measurements may not be reliable In operation, as shown in FIG. 3A, after exiting connector 212, the OCT beam 214 is collimated, preferably using a collimating optical fiber 196. Following collimating fiber 196 the OCT beam 214 is directed to an z-scan device 193 operable to change the focal point of the OCT beam in a z-direction, and x- and y-scan devices 195 and 197, which are operable to scan the OCT beam in x and y-directions perpendicular to the z-direction.

Following the collimating optical fiber 196, the OCT beam 214 continues through a z-scan device 193, 194. Preferably, the z-scan device is a Z telescope 193, which is operable to scan focus position of the laser pulse beam 66 in the patient's eye 101 along the Z axis. For example, the Z-telescope can include a Galilean telescope with two lens groups (each lens group includes one or more lenses). One of the lens groups moves along the Z axis about the collimation position of the Z-telescope 193. In this way, the focus position in the patient's eye 101 moves along the Z axis. In general, there is a relationship between the motion of lens group and the motion of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as a z-scan device for changing the focus point of the OCT beam 214 in the patient's eye 101. The Z-scan device can be controlled automatically and dynamically by the controller 60 and selected to be independent or to interplay with the X and Y scan devices described next.

After passing through the z-scan device, the OCT beam 214 is incident upon an X-scan device 195, which is operable to scan the OCT beam 214 in the X direction, which is dominantly transverse to the Z axis and transverse to the direction of propagation of the OCT beam 214. The X-scan device 195 is controlled by the controller 60, and can include suitable components, such as a lens coupled to a MEMS device, a motor, galvanometer, or any other well-known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 196, the OCT beam 214 is incident upon a Y scan device 197, which is operable to scan the OCT beam 214 in the Y direction, which is dominantly transverse to the X and Z axes. The Y-scan device 197 is controlled by the controller 60, and can include suitable components, such as a lens coupled to a MEMS device, motor, galvanometer, or any other well-known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 195 and the Y-Scan device 197 can be provided by an XY-scan device configured to scan the laser pulse beam 66 in two dimensions transverse to the Z axis and the propagation direction of the laser pulse beam 66. The X-scan and Y scan devices 195, 197 change the resulting direction of the OCT beam 214, causing lateral displacements of OCT beam 214 located in the patient's eye 101.

The OCT sample beam 214 is then directed to beam splitter 173 through lens 175 through quarter wave plate 171 and aperture 114 and to the patient eye 101. Reflections and scatter off of structures within the eye provide return beams that retrace back through the patient interface quarter wave plate 171, lens 175, beam splitter 173, y-scan device 197, x-scan device 195, z-scan device 193, optical fiber 196 and beam combiner 204 (FIG. 3), and back into the OCT detection device 220. The returning back reflections of the sample arm 201 are combined with the returning reference portion 206 and directed into the detector portion of the OCT detection device 220, which generates OCT signals in response to the combined returning beams. The generated OCT signals that are in turn interpreted by the controller 60 to determine the spatial disposition of the structures of interest in the patient's eye 101. The generated OCT signals can also be interpreted by the controller to determine the spatial disposition of the structures of interest in the patient's eye 101. The generated OCT signals can also be interpreted by the control electronics to align the position and orientation of the patient eye within the patient interface.

The optical measurement systems according to the present invention preferably comprise an iris imaging subsystem 40. The imaging subsystem 40 generally comprises an infrared light source, preferably infrared light source 152, and detector 141. In operation light from the light source 152 is directed along second optical path 160 to first optical path 170 and is subsequently directed to eye 101 as described above. Light reflected from the iris of eye 101 is reflected back along first optical path 170 to detector 141. In normal use, an operator will adjust a position or alignment of system 100 in XY and Z directions to align the patient according to the image detector array 141. In one embodiment of the iris imaging subsystem 40, eye 101 is illuminated with infrared light from light source 152. In this way, the wavefront obtained by wavefront sensor 155 will be registered to the image from detector array 141.

The image that the operator sees is the iris of eye 100. The cornea generally magnifies and slightly displaces the image from the physical location of the iris. So the alignment that is done is actually to the entrance pupil of the eye. This is generally the desired condition for wavefront sensing and iris registration.

Iris images obtained by the iris imaging subsystem may be used for registering and/or fusing the multiple data sets obtained by the various subsystems of the present invention, by methods described for instance in "Method for registering multiple data sets," U.S. patent application Ser. No. 12/418,841, which is incorporated herein by reference. As set forth in application Ser. No. 12/418,841, wavefront aberrometry may be fused with corneal topography, optical coherence tomography and wavefront, optical coherence tomography and topography, pachymetry and wavefront, etc. For instance, with image recognition techniques it is possible to find the position and extent of various features in an image. Regarding iris registration images, features that are available include the position, size and shape of the pupil, the position, size and shape of the outer iris boundary (OIB), salient iris features (landmarks) and other features as are determined to be needed. Using these techniques, both patient movement between measurements (and/or during a measurement sequence) can be identified, as well as changes in the eye itself (including those induced by the measurement, such as changes in the size of the pupil, changes in pupil location, etc.).

In many embodiments, an optical measurement system according the present includes a target fixation subsystem 150 (FIG. 1), and an assembly 100 shown in FIGS. 3A and 3B includes fixation target subsystem 180 which includes a fixation target 182 for the patient to view. Fixation target subsystem 180 is used to control the patient's accommodation, because it is often desired to measure the refraction and wavefront aberrations when eye 100 is focused at its far point (e.g., because LASIK treatments are primarily based on this). In the target fixation subsystem, a projection of a target, for instance a cross-hair pattern is projected onto the eye of the patient, the cross hair pattern being formed by a backlit LED and a film.

In operation, light originates from the light source 152 or, alternatively, from video target backlight 182 and lens 186. Lens 185 collects the light and forms an aerial image T2. This aerial image is the one that the patient views. The patient focus is maintained on aerial image 182 during measurement so as to maintain the eye in a fixed focal position.

The operating sequence the optical measurement system and methods of the present is not particularly limited. A scan of the patient's eye may comprise one or more of a wavefront aberrometry measurement of a patient's eye utilizing the wavefront aberrometry subsystem, a corneal topography measurement of a patient's eye and an OCT scan of the patient's eye using the OCT subsystem, wherein the OCT scan includes a scan at each or one or more locations within the eye of the patient. These locations of the OCT scan may correspond to the location of the cornea, the location of the anterior portion of the lens, the location of the posterior portion of the lens and the location of the retina. In a preferred embodiment, the operating sequence includes each of a wavefront aberrometry measurement, a corneal topography measurement and an OCT scan, wherein the OCT scan is taken at least at the retina, the cornea and one of anterior portion of the patient's lens. Preferably, an iris image is taken simultaneously with or sequentially with an each of measurements taken with wavefront aberrometry subsystem the corneal topography subsystem and the OCT subsystem, including an iris image take simultaneously with or sequentially with the location of each OCT scan. This results in improved accuracy in the 3-dimensional modeling of the patient's eye by permitting the various data sets to be fused and merged into a 3-dimensional model.

Figure 8:
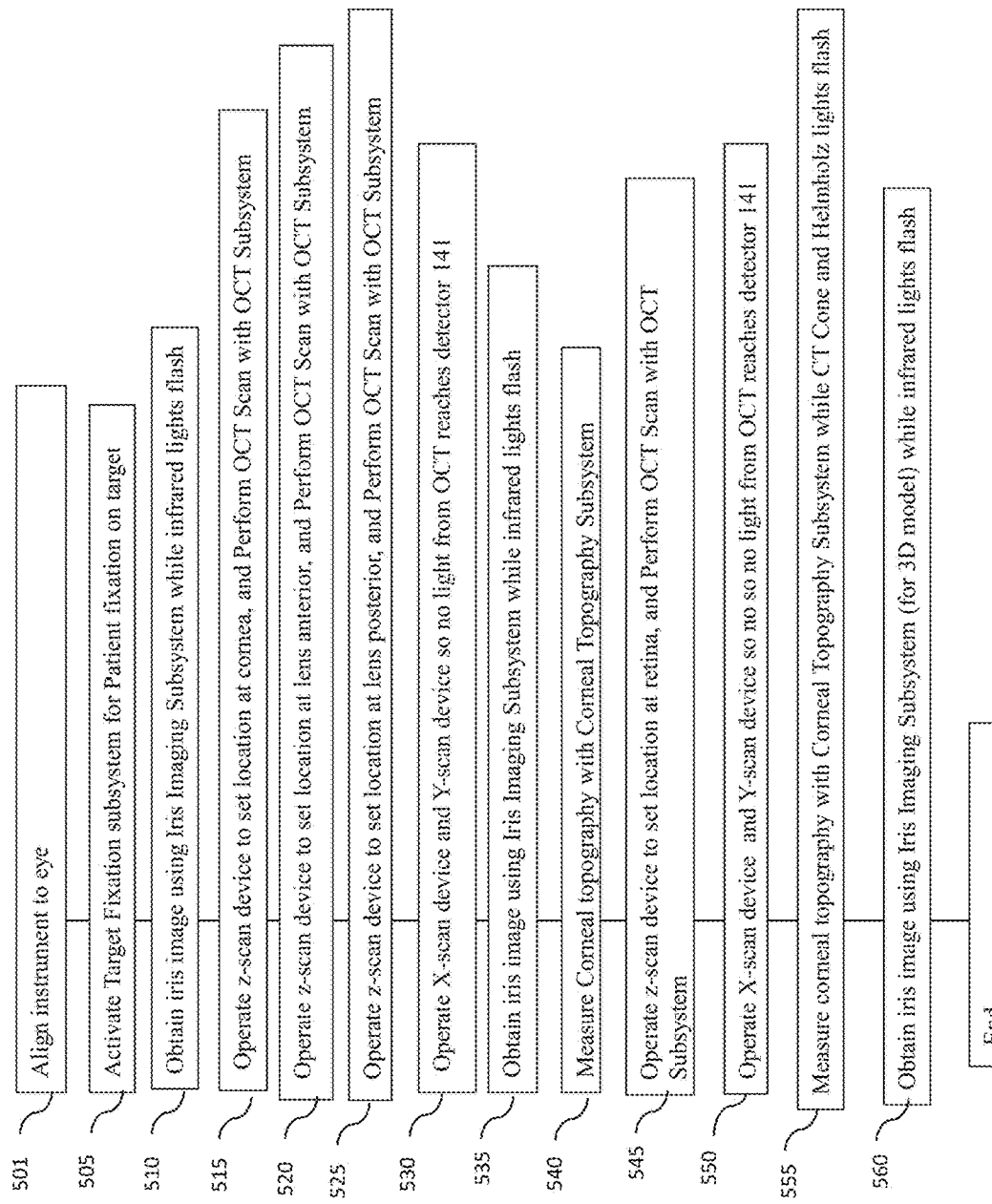
FIG. 8 is a flowchart of an example embodiment of a method for measuring one or more characteristics of an eye with an optical measurement instrument according to one embodiment described herein, including wavefront aberrometry, corneal topography and OCT measurements at various locations with the eye along the axial length of the eye.

FIG. 8 shows one embodiment of an operating sequence and method in which wavefront aberrometry measurements, corneal topography measurements and OCT measurements are all taken. The optical measurement apparatus, including the method of FIG. 8 may be used preoperatively, intra-operatively and/or postoperatively. In the method of FIG. 8, a step 501 comprises aligning the optical measurement system to the eye of the patent. A step 505 comprises activating the Target Fixation subsystem for patient fixation on target. A step 510 comprises activating the wavefront aberrometer subsystem such that the wavefront aberrometer light source 510 is activated and the eye refraction is measured via the wavefront sensor. A step 515 comprises activating the target fixation system to move the target to an optimum position and activate the wavefront aberrometer subsystem such that the wavefront aberrometer light source 152 is activated and the eye refraction is measured via the wavefront sensor 155. A step 520 comprises obtaining an iris image using Iris Imaging Subsystem while infrared light source 152 is operating. A step 525 comprises operating the z-scan device to set OCT scan location at or near cornea, and performing an OCT Scan with the OCT Subsystem. A step 530 comprises operating the z-scan device to set the OCT location at a location at or near the lens anterior and performing an OCT Scan with the OCT Subsystem. A step 535 comprises operating the z-scan device to set the OCT location at a location at or near the lens posterior and performing an OCT Scan with the OCT Subsystem. A step 540 comprises operating the X-scan device and Y-scan device so no light from OCT reaches detector 141. A step 545 comprises obtaining an iris image using the Iris Imaging Subsystem while the infrared light source 152 flashes. A step 550 comprises obtaining an iris image using the his Imaging Subsystem while the light sources 120 and Helmholz source flash. A step 550 comprises measuring the corneal topography with the Corneal Topography Subsystem. A step 555 comprises operating the z-scan device to set the OCT location at a location at or near the retina and performing an OCT Scan with the OCT Subsystem. A step 560 comprises operating the X-scan device and Y-scan device so no light from OCT reaches detector 141. An optional step 565 comprises measure corneal topography with Corneal Topography Subsystem, which may provide for an improved 3D model of the patient eye. An optional step 570 comprises obtaining an iris image using his Imaging Subsystem (for 3D model).

Figure 9:
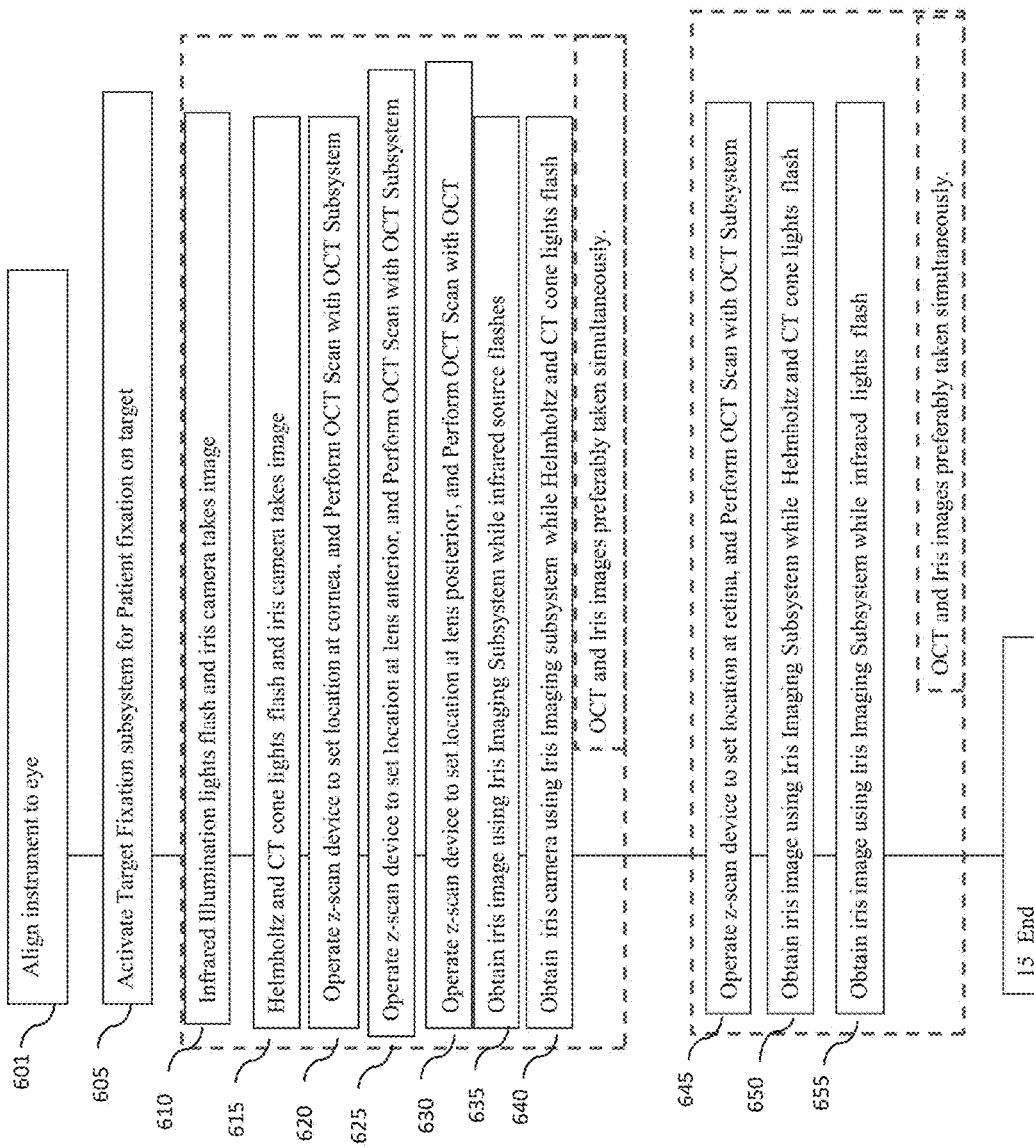
FIG. 9 is a flowchart of another example embodiment of a method for measuring one or more characteristics of an eye with an optical measurement instrument.

FIG. 9 shows one embodiment of an operating sequence and method in which no wavefront aberrometry measurements are taken. The optical measurement apparatus, including the method of FIG. 8 may be used preoperatively, intra-operatively and/or postoperatively. In the embodiment of FIG. 9, a step 601 comprises aligning the optical measurement system to the eye of the patent. A step 605 comprises activating the Target Fixation subsystem for patient fixation on target. A step 610 comprises obtaining an iris image using his Imaging Subsystem while infrared light source 152 is operating. A step 615 comprises operating the z-scan device to set OCT scan location at or near cornea, and performing an OCT Scan with the OCT Subsystem. A step 620 comprises operating the z-scan device to set the OCT location at a location at or near the lens anterior and performing an OCT Scan with the OCT Subsystem. A step 625 comprises operating z-scan device to set the OCT location at a location at or near the lens posterior and performing an OCT Scan with the OCT Subsystem. A step 530 comprises operating the X-scan device and Y-scan device so no light from OCT reaches detector 141. A step 635 comprises obtaining an iris image using the Iris Imaging Subsystem while the infrared light source 152 flashes. A step 640 comprises measuring the corneal topography with the Corneal Topography Subsystem. A step 645 comprises operating the z-scan device to set the OCT location at a location at or near the retina and performing an OCT Scan with the OCT Subsystem. A step 650 comprises operating the X-scan device and Y-scan device so no light from OCT reaches detector 141. An optional step 655 comprises measure corneal topography with Corneal Topography Subsystem, which may provide for an improved 3D model of the patient eye. An optional step 660 comprises obtaining an iris image using Iris Imaging Subsystem.

Figure 10:
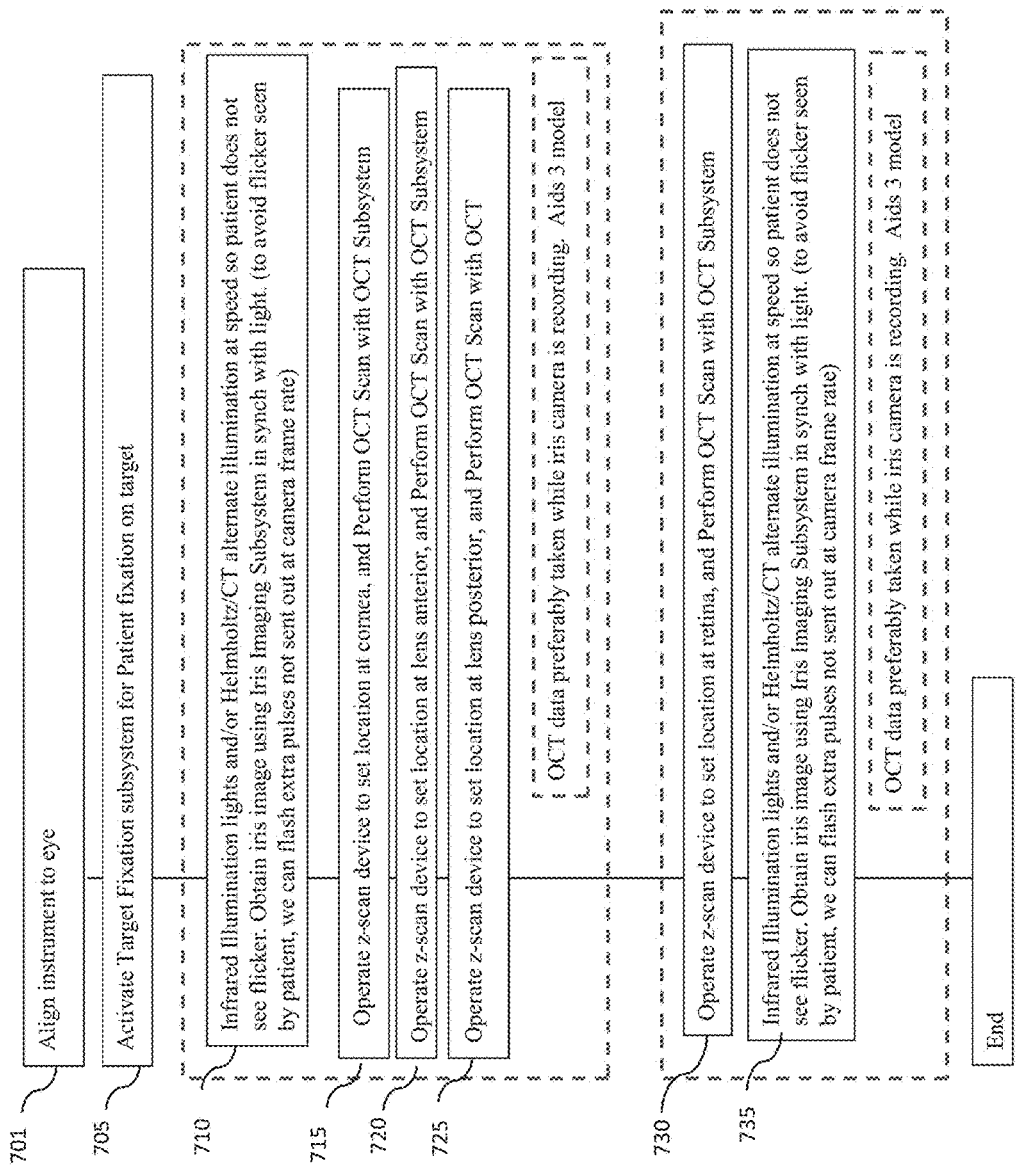
FIG. 10 is a flowchart of another example embodiment of a method for measuring one or more characteristics of an eye with an optical measurement instrument in which OCT measurements and iris imaging may be performed simultaneously.

FIG. 10 shows an embodiment of an operational sequence and method in which OCT measurements utilizing the OCT subsystem and Iris images using the iris imaging subsystem may be taken simultaneously in order to improve three dimensional modeling of the patient's eye and improved iris registration of the measurement data sets. The operational sequence of FIG. 10 may be applied to or incorporated into either of the operational sequences and methods of FIG. 8 or 9 as would be readily understood by those ordinarily skilled. In order to effectuate the operating sequence and method of FIG. 10, a lens is inserted into optical path 170 between beam splitter 173 and detector 141. The inserted lens is selected to preferentially pass infrared light used for iris imaging but to block an OCT beam from the OCT light source from reaching detector 141. In this configuration, OCT measurements and iris images may be taken simultaneously. Further, in the embodiment of FIG. 10 a regular speed global shutter iris camera is used operating at 12 frames/second. The operating sequence and method of FIG. 10 may be used preoperatively, intra-operatively and/or postoperatively.

In the embodiment of FIG. 10, a step 701 comprises aligning the optical measurement system to the eye of the patent. A step 705 comprises activating the Target Fixation subsystem for patient fixation on target. A step 710 comprises obtaining an iris image using his Imaging Subsystem while infrared light source 152 is operating. A step 715 comprises obtaining an iris image using Iris Imaging Subsystem while corneal topography light sources 120 and Helmholz light source 132 are operating. A step 720 comprises operating the z-scan device to set OCT scan location at or near cornea, and performing an OCT Scan with the OCT Subsystem. A step 725 comprises operating the z-scan device to set the OCT location at a location at or near the lens anterior and performing an OCT Scan with the OCT Subsystem. A step 730 comprises operating z-scan device to set the OCT location at a location at or near the lens posterior and performing an OCT Scan with the OCT Subsystem. A step 735 comprises obtaining an iris image using Iris Imaging Subsystem while infrared light source 152 is operating. A step 740 comprises obtaining an iris image using Iris Imaging Subsystem while corneal topography light sources 120 and Helmholz light source 132 are operating. A step 745 comprises operating the z-scan device to set the OCT location at a location at or near the retina and performing an OCT Scan with the OCT Subsystem. A step 750 comprises obtaining an iris image using Iris Imaging Subsystem while corneal topography light sources 120 and Helmholz light source 132 are operating. A step 755 comprises obtaining an iris image using his Imaging Subsystem while infrared light source 152 is operating.

Figure 11:
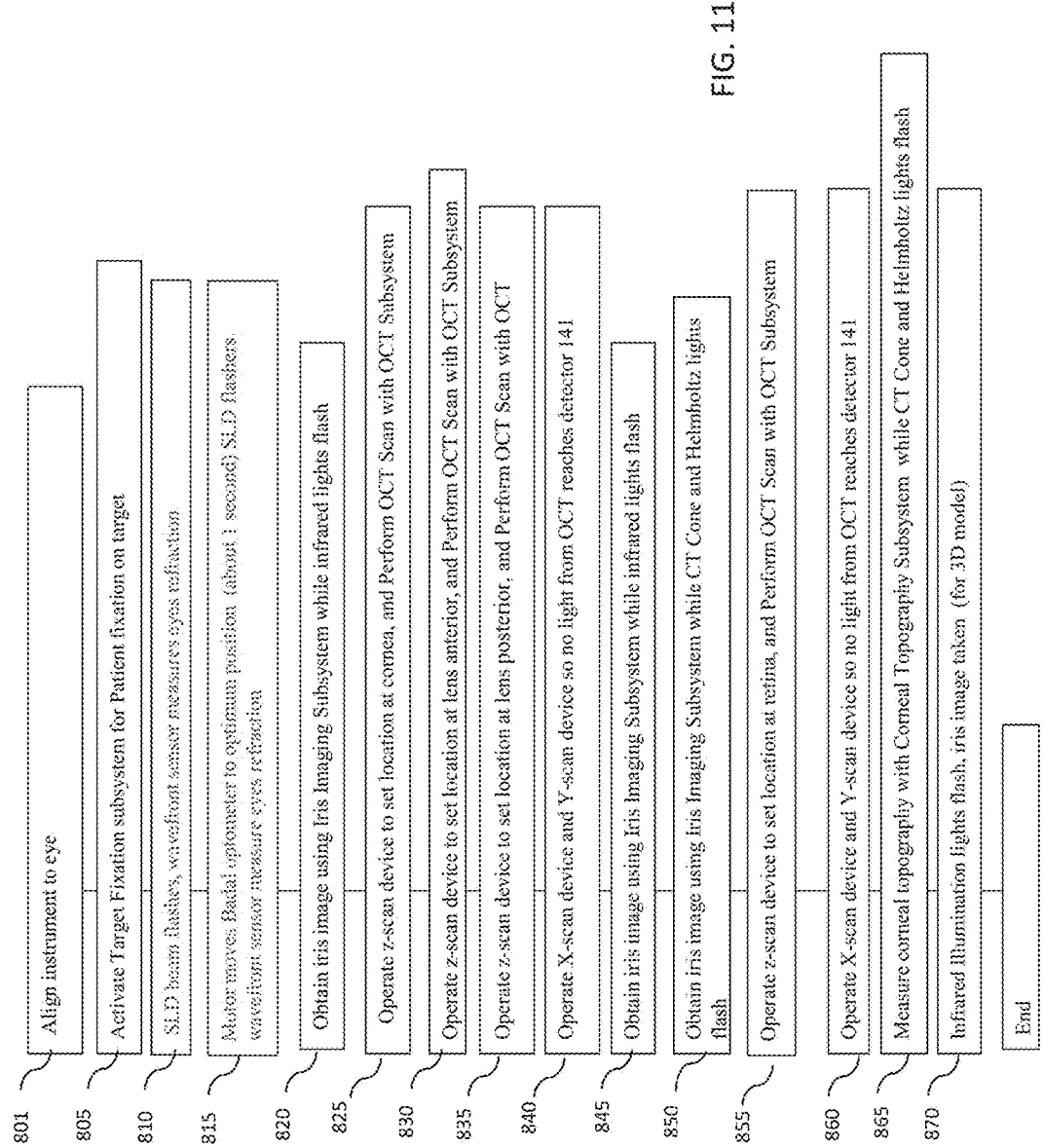
FIG. 11 is a flowchart of yet another example embodiment of a method for measuring one or more characteristics of an eye with an optical measurement instrument in which OCT measurements and iris imaging may be performed simultaneously

FIG. 11 shows another embodiment of an operational sequence and method in which OCT measurements utilizing the OCT subsystem and Iris images using the iris imaging subsystem may be taken simultaneously in order to improve three dimensional modeling of the patient's eye and improved iris registration of the measurement data sets. The operational sequence of this embodiment may be applied to or incorporated into either of the operational sequence and methods of FIG. 8 or 9 as would be readily understood by those ordinarily skilled. As with the method of FIG. 10, in order to effectuate the operating sequence and method of FIG. 11, a lens is inserted into optical path 170 between beam splitter 173 and detector 141. The inserted lens is selected to preferentially pass infrared light used for iris imaging but to block an OCT beam from the OCT light source from reaching detector 141. In this configuration, OCT measurements and iris images may be taken simultaneously. Further, in the embodiment of FIG. 10 a high speed global shutter iris camera, or fast frame rate, is used operating at 60 frames/second. Under the fast frame rate conditions of this embodiment, an infrared illumination source, such as a wavefront aberrometry source, may be used with one or more second light sources, such as a combination of the corneal topography sources 120 and the Helmholz source, to alternately illuminate a patient's eye repeatedly at short intervals (i.e., alternative short flashes). Under these conditions, the iris imaging subsystem may be synched to the flash from each source so as to capture iris images under both illumination conditions. The operating sequence and method of FIG. 11 may be used preoperatively, intra-operatively and/or postoperatively.

In the embodiment of FIG. 11, a step 801 comprises aligning the optical measurement system to the eye of the patient. A step 805 comprises activating the Target Fixation subsystem for patient fixation on target. A step 810 comprises obtaining an iris image using his Imaging Subsystem while infrared light source 152 is operating and obtaining an iris image using his Imaging Subsystem while corneal topography light sources 120 and Helmholz light source 132 are operating. This is done by alternately operating the infrared light source and a combination of the corneal topography/Helmholz light sources so as to alternately illuminate the patient's eye with the infrared light source and the combined light sources, preferably at a rate that a patient's eye cannot resolve the "flicker." In this step, the Iris imaging subsystem is in synch with the respective illuminate lights. A step 815 comprises operating the z-scan device to set OCT scan location at or near cornea, and performing an OCT Scan with the OCT Subsystem. A step 820 comprises operating the z-scan device to set the OCT location at a location at or near the lens anterior and performing an OCT Scan with the OCT Subsystem. A step 825 comprises operating z-scan device to set the OCT location at a location at or near the lens posterior and performing an OCT Scan with the OCT Subsystem. A step 830 comprises operating the z-scan device to set the OCT location at a location at or near the retina and performing an OCT Scan with the OCT Subsystem. A step 835 comprises obtaining an iris image using Iris Imaging Subsystem while infrared light source 152 is operating and obtaining an iris image using Iris Imaging Subsystem while corneal topography light sources 120 and Helmholz light source 132 are operating as described above for Step 810.

The optical measurement instrument 1 and the optical measurements obtained therewith may be used pre-operatively, i.e. before a cataract surgery or other surgical procedure, for, e.g., eye biometry and other measurements, diagnostics and surgical planning. Surgical planning may include one or more predictive models. In the one or more predictive models, one or more characteristics of the postoperative condition of the patient's eye or vision is modeled based on one or more selected from the group consisting of pre-operative measurements obtained from the optical measurement instrument 1, a contemplated surgical intervention, and on or more algorithms or models stored in the memory of the optical measurement system 1 and executed by the processor. The contemplated surgical intervention may include the selection of an IOL for placement, the selection of an IOL characteristic, the nature or type of incision to be used during surgery (e.g., relaxation incision), or one or more post-operative vision characteristics requested by the patient.

The optical measurement instrument 1 and the optical measurements obtained therewith may be used intra-operatively, e.g., during a cataract surgery or other surgical procedure, for, e.g., intraoperative eye diagnostics, determining IOL placement and position, surgical planning, and control/or of a laser surgical system. For instance, in the case of laser cataract surgical procedure, any measurement data obtained preoperatively by the optical measurement instrument may be transferred to a memory associated with a cataract laser surgical system for use before, during or after either the placement of a capsulotomy, fragmentation or a patient's lens or IOL placement during the cataract surgery. In some embodiments, measurements using optical measurement instrument 1 may be taken during the surgical procedure to determine whether the IOL is properly placed in the patient's eye. In this regard, conditions measured during the surgical procedure may be compared to a predicted condition of the patient's eye based on pre-operative measurements, and a difference between the predicted condition and the actual measured condition may be used to undertake additional or corrective actions during the cataract surgery or other surgical procedure.

The optical measurement instrument 1 and the optical measurements obtained therewith may be used postoperatively, i.e., after a cataract surgery or other surgical procedure, for, e.g., post-operative measurement, postoperative eye diagnostics, postoperative IOL placement and position determinations, and corrective treatment planning if necessary. The postoperative testing may occur sufficiently after the surgery that the patient's eye has had sufficient time to heal and the patient's vision has achieved a stable, postsurgical state. A postoperative condition may be compared to one or more predicted condition performed pre-operatively, and a difference between the preoperatively predicted condition and the postoperatively measured condition may be used to plan additional or corrective actions during the cataract surgery or other surgical procedure.

The optical measurement instrument 1, including the corneal topography subsystem, the OCT subsystem and the wavefront aberrometry subsystem, utilizing a suitable operating sequence as disclosed herein, is operable to measure one, more than one or all of the following: ocular biometry information, anterior corneal surface information, posterior corneal surface information, anterior lens surface information, posterior lens surface information, lens tilt information and lens position information. In some embodiments, the ocular biometry information may include a plurality of central corneal thicknesses (CCT), an anterior chamber depth (ACT), a pupil diameter (PD), a white to white distance (WTW), a lens thickness (LT), an axial length (AL) and a retinal layer thickness. This measurement data may be stored in memory 62 associated with controller 60. The plurality of characteristics may be measured preoperatively, and where appropriate, intra-operatively, and postoperatively.

As noted above, it would be desirable to improve the Chromatic Adjustment Factor (CAF) value used with aberrometer measurements so that the calculated visible refraction matches better to the manifest refraction that an optometrist would determine with a phoropter. Embodiments of methods and systems which may accomplish this are now described.

The present inventors have theorized that variations in the structure of each eye prevent a "one-size-fits-all" CAF from consistently giving good results. The present inventors have determined that, instead, CAF should be based on detailed knowledge of the structure of the particular eye being measured.

Components of optical measurement instrument 1 may be employed to measure many of the structural characteristics of the eye that should be measured to obtain a custom CAF for the eye. The items of interest and the measurement systems/methods appear in Table 1 below:

TABLE 1

| Item | Measurement Method |
| --- | --- |
| Refraction in Infrared | Aberrometer |
| Anterior Corneal Radius | Corneal Topographer |
| Anterior Chamber Depth | Optical Coherence Tomographer (OCT) |
| Axial Length of Eye (Total) | OCT |
| Lens Power | Calculations (Described Below) |
| Posterior Corneal Radius | PURKINJE (Described Below) |
| Anterior Chamber Depth | OCT |
| Corneal Thickness | OCT |
| Lens Thickness | OCT |

TABLE 1-continued

| Item | Measurement Method |
| --- | --- |
| Lens Anterior Radius | PURKINJE |
| Lens Posterior Radius | PURKINJE |

Beneficially, optical measurement instrument makes it possible to combine all these measurement techniques and methodologies into a single instrument.

Figure 15:
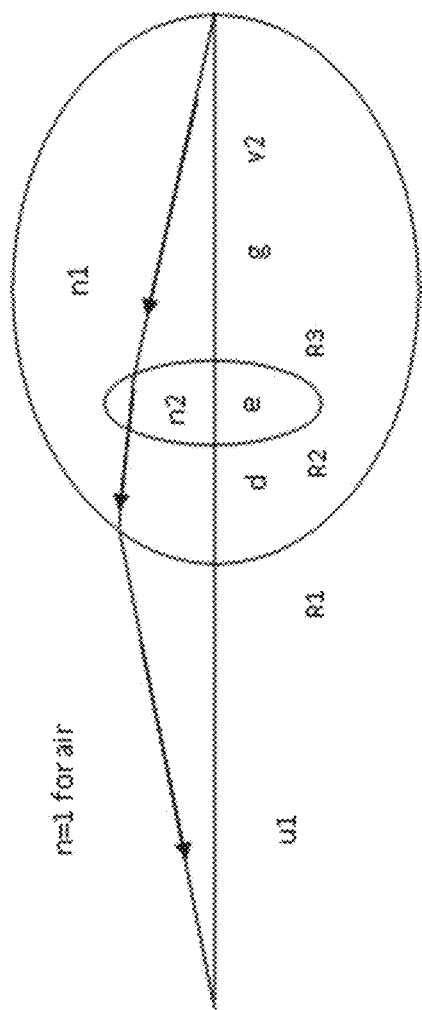
FIG. 15 shows a simplified eye model.

FIG. 15 shows a simplified eye model 1500 from G. Smith and A. Atchison, "*The Eye and visual optical instruments,*" CAMBRIDGE UNIVERSITY PRESS, 1996, Appendix A. ("Smith and Atchison")

Eye model 1500 consists of a cornea with only an anterior surface, a lens suspended in a fluid, and the retina. In a real eye, the cornea has two surfaces and the total power of the cornea is the sum of the front and back surface powers. For instance, in the Le Grand Full Theoretical Eye, the front corneal surface has a power of 48 diopters and the posterior surface has a power of −6 diopters. The total corneal power is 42 diopters. But for the Le Grand Simplified Eye, the two layer cornea is replaced with single layer cornea that has a curvature such that its power is 42 diopters.

In FIG. 15, an infrared probe beam (not shown) enters the cornea from the left, travels through the lens and then hits the retina. Most of the light is absorbed, but some is scattered back toward the left. The scattered light is drawn with arrows. The aberrometer collects the light leaving the cornea and from that calculates the quantity u1. The infrared refraction of the eye is simply $S(ir)=1/u1$.

The quantities in the figure are described below.

u1 is the distance where the infrared ray from the retina crosses the optical axis (object distance)

v2 is the distance from the lens to an image, where the infrared ray from the on-axis object point R1 is the simplified radius of the cornea. (see discussion below)

R2 is the radius of the anterior of the lens

R3 is the radius of the posterior of the lens n1 is the index of refraction in the media surrounding the lens (from Smith and Atchison, naqueous)

n2 is the index of refraction of the lens (from Smith and Atchison)

d is the distance between the cornea and the lens (anterior chamber depth)

e is the thickness of the lens g is the distance between the lens and retina (posterior chamber depth)

FIG. 15 is drawn with g=v2 because that is the specific case we have when an aberrometer is measuring the infrared refraction of an eye. Also, FIG. 15 shows that the axial length of the eye is d+e+g. OCT measurements typically provide all of these lengths.

In this treatment, the lens is treated as a thin lens. We therefore do not need the values of the lens anterior and posterior radii, and we assume a lens thickness of zero. Also, Smith and Atchison, cited above, shows that the indices are virtually the same for the media in front and behind the lens. Then using paraxial theory, we can derive a formula for the lens power $P_{LENS}$:

$$P_{lens}=1/(g*(d-(f1*u1)/(u1-f1))/(d+g-(f1*u1)/(u1-f1))) \quad (1)$$

The quantities on the right hand side may be founds as follows:
- u1 measured by aberrometer
- g measured by OCT
- d measured by OCT
- f1 from formula f1=R1/(n1−1)
- n1 is index of refraction of media surrounding the lens (naqueous in Smith and Atchison)

$$R1=1.0256*ACR$$

ACR is anterior corneal radius measured by a topographer

The value of R1 used in this formula is not the same as the anterior corneal radius measured by the topographer. Here we have adopted the same procedure that Le Grand used where the two surface cornea is replaced with a single surface of reduced curvature.

Of course, if data is available on the posterior corneal radius (PCR), it would be preferable use this data to calculate a more customized value of R1. Then the value for the simplified corneal radius is:

$$R1=(n1-1)/(P_{ANTERIOR}+P_{POSTERIOR}) \quad (2)$$

where $P_{ANTERIOR}=(ncomea-1)/ACR$ and $P_{POSTERIOR}=(n1-ncornea)/PCR$.

Once the lens power is known along with the simplified corneal radius, anterior chamber depth and posterior chamber depth, there are at least two approaches for determining a customized CAF factor: ray tracing or correlation to clinical data.

The first approach of ray tracing is a standard mathematical technique commonly used in geometrical optics. To calculate a customized CAF, we follow this procedure.

Start with infrared ray from the scattering layer in the retina, on the optical axis, with any non-zero angle.

Trace the infrared ray from the retina, through the posterior chamber, through the thin lens, through the anterior chamber, and then through the cornea.

Calculate the distance u1 where the infrared ray crosses the optical axis

Next, originate a visible ray at distance dX in front of the scattering layer in the retina, on the optical axis with any non-zero angle. (dX has value of 0.08 mm and represents the distance between the infrared scatter layer and the photoreceptors)

Trace the visible ray from the retina, through the lens, and through the cornea.

Calculate the distance u2 where the visible ray crosses the optical axis

Calculate the value CAF=1/u1−1/u2

Calculate the visible refraction from S(vis)=S(ir)−CAF

The value of dX can be adjusted for a particular eye model that is being used. For instance, with the emmetropic Le Grand eye, if we assume the infrared scatter layer and photoreceptors are co-located, the predicted difference between the infrared and the calculated visible refractions is 0.89 diopters. This is larger than the clinically observed difference between infrared and manifest refractions for an average emmetrope of 0.7 diopters. If the value of dX is set to 0.08 mm, the Le Grand eye then matches the clinically observe difference of 0.7 diopters.

In the ray tracing method described above, we used a "simplified" eye model. However, this method of calculating the CAF can be modified to take advantage of additional structural parameters if they are known. For instance, corneal thickness, lens thickness, and lens radii could be included. However, ray tracing studies have shown that if these quantities are not known, we can assume average published values for them with relatively small impact on the calculated CAF.

The second approach of calculating a customized CAF would be by comparison to clinical data. The essential steps of such an approach are outlined below:

Collect data on large group of subjects including these measurements:
- Infrared refraction
- Anterior corneal radius
- Anterior chamber depth
- Axial length
- Lens power
- Manifest refractions (measured by optometrist with a phoropter)

Analyze data set to determine formulas for the CAF value that would improve calculation of visible refractions. The best formula would be the one that resulted in the lowest deviation of the calculated visible refractions from manifest refractions.

For example, one potential formula would be:

$$CAF=0.7+K1*P_{CORNEA}/P_{LENS}+K2*S(ir) \quad (3)$$

Where:
- CAF=chromatic adjustment factor
- K1=a constant determined by analysis of the data set
- $P_{CORNEA}$=the power of the cornea=(n1−1)/R1 where n1 is the index of the cornea and R1 is the anterior a radius of the cornea
- $P_{LENS}$=power of the lens
- K2=a constant determined by analysis of the data set
- S(ir)=infrared refraction measured by the aberrometer The factor K2 is included because theoretical raytracing indicates a general trend that more myopic eyes have larger CAF values. This observation has been included in papers by many previous researchers, including Atchison and Smith.

Another formula likely to give good results would be:

$$CAF=K3+K4*P_{CORNEA}K5*P_{LENS}+K6*S(ir) \quad (4)$$

The constants K3, K4, K5 and K6 would be found by analysis of the data set.

For each patient, the relationship between CAF and the calculated visible refraction S(vis) is:

$$S(vis)=S(ir)-CAF \quad (5)$$

Other formulas for the CAF are possible as well. For instance, terms including factors such as of anterior chamber depth, posterior chamber depth, or posterior corneal radius could be added. Ray tracing done on schematic model eyes with programs such as ZEMAX indicate that simple linear equations are likely to provide good matches to clinical data.

FIG. 12 is a flowchart of an example embodiment of a method 1200 for measuring a chromatically corrected refraction of a subject's eye using an optical measurement system or instrument such as optical measurement instrument 1.

An operation 1210 includes using a probe beam having an infrared wavelength in the infrared spectrum to measure a refraction of the subject's eye at the infrared wavelength. In particular operation 1210 may include measuring a refraction of a subject's eye with an aberrometer which includes a Shack-Hartmann wavefront sensor. In some embodiments, the infrared light may have a wavelength of 840 nm, or about 840 nm.

An operation 1220 includes capturing at least two different Purkinje images at two different corresponding wavelengths from at least one surface of the lens of the subject's eye.

In some embodiments, method 1200 may be performed using optical measurement instrument 1 of FIGS. 1A-C and 2, and/or assembly 100 of FIGS. 3A and 3B. In that case, a light pattern generator 1275 may be employed to generate the light at two different wavelengths which is directed onto the subject's eye to produce the Purkinje images, and iris camera 1285 may be employed as an image detector configured to capture the at least two different Purkinje images at the two different wavelengths from at least one surface of the lens of the subject's eye. In some embodiments, iris camera 1285 may be included in iris imaging subsystem 40.

Figure 13:
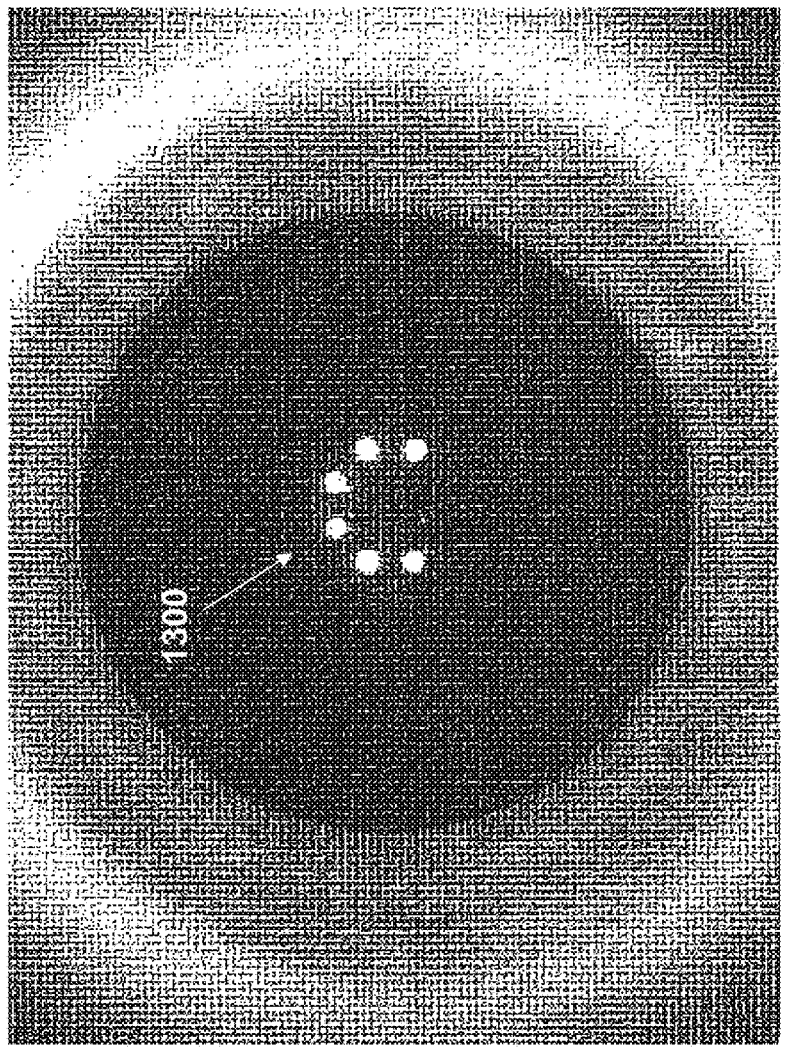
FIG. 13 illustrates an example Purkinje image from an eye.

FIG. 13 illustrates an example Purkinje image 1300.

In various embodiments, the Purkinje images may include Purkinje III images from the anterior surface of the lens of the eye and/or Purkinje IV images from the posterior surface of the lens. In various embodiments, one of the two wavelengths at with the Purkinje images is captured is the same, or substantially the same, as the infrared wavelength of the probe beam in refraction measurement of operation 1210, for example 840 nm. In some embodiments, the other wavelength is in the visible spectrum, for example in the green part of the visible spectrum (e.g., 550 nm or about 550 nm). In other embodiments, the other wavelength is in the infrared spectrum, for example 780 nm. In some embodiments, operation 1220 includes capturing at least two different Purkinje images at three (or more) different corresponding wavelengths—for example two different infrared wavelengths (e.g., 840 nm and 780 nm) and one visible wavelength (e.g., 550 nm). This may improve the accuracy of a subsequent operation of determining a customized chromatic adjustment factor (CAF) for the subject's eye. When only two wavelengths in the infrared spectrum are employed, the custom CAF may be obtained by extrapolating results from the two infrared wavelengths to extend into the visible spectrum, for example at a frequency of 550 nm.

An operation 1230 includes determining from the at least two different Purkinje images a value for at least one parameter of the subject's eye. In some embodiments, this may include measuring the curvature of the cornea of the subject's eye, (for example using a corneal topographer), and determining from the measured curvature of the cornea and at least two Purkinje III images a change in an index of refraction of the cornea from the infrared wavelength to the visible wavelength. In particular, the apparent location and size of the Purkinje III image will change from the infrared wavelength to the visible wavelength.

Figure 14:
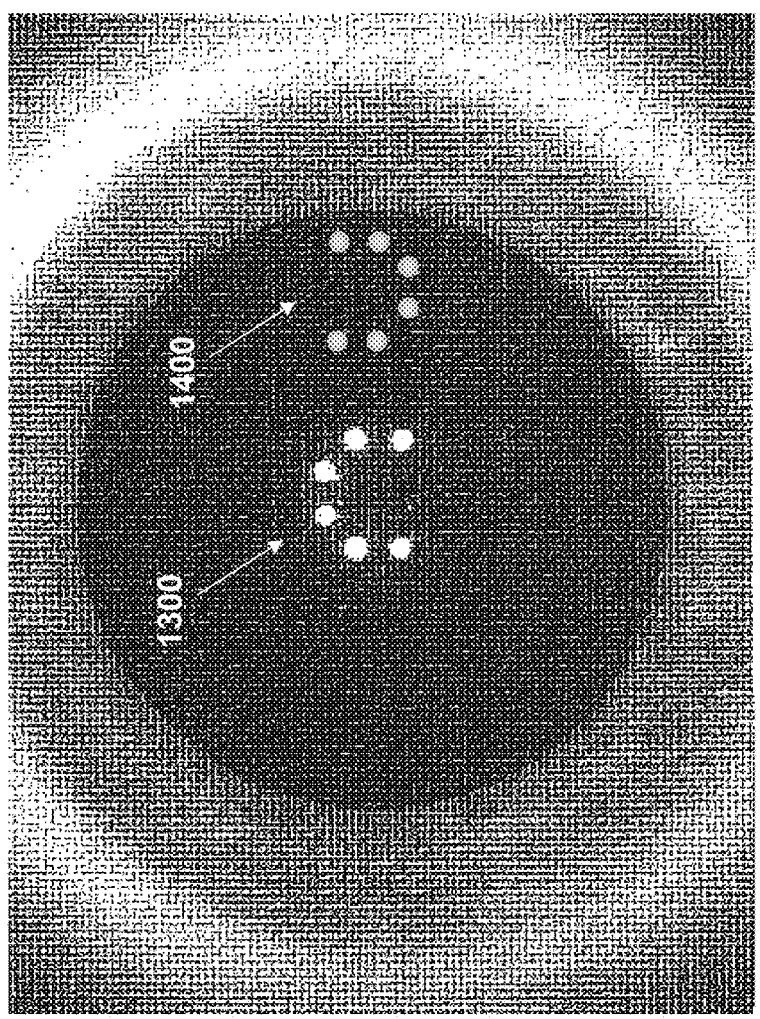
FIG. 14 illustrates an example of two Purkinje images from an eye.

FIG. 14 illustrates an example of two Purkinje images 1300 and 1400 from an eye. Here the Purkinje image 1300 may be a Purkinje III image from the anterior of the lens, and Purkinje image 1400 may be a Purkinje III image from the posterior of the lens.

In some embodiments, operation 1230 may include determining from at least two Purkinje III images and at least two Purkinje IV images a change in the index of refraction of the lens of the eye from the infrared wavelength where the refraction measurement was made, to a visible wavelength in the visible light spectrum. In some embodiments, operation 1230 may include determining from at least two Purkinje IV images the radius of curvature of the posterior surface of a lens of the eye. In some embodiments, operation 1230 may include determining from at least two Purkinje III images the radius of curvature of the anterior surface of a lens of the eye.

In some embodiments, method 1200 may include an optional operation of employing an optical coherence tomographer to measure the thickness of the lens of an eye, and using the measured thickness of the lens and the Purkinje IV images from the posterior surface of the lens to determine the customized chromatic adjustment factor for the eye.

An operation 1240 includes using the value of the at least one parameter to determine a customized chromatic adjustment factor (CAF) for the subject's eye. In some embodiments, this may include performing ray tracing using an eye model including the at least one parameter, wherein the value for the at least parameter is employed in the ray tracing. In some embodiments, this may include solving a linear equation wherein at least one variable in the linear equation corresponds to the at least one parameter, wherein solving the linear equation includes substituting the value for the at least one variable in the linear equation.

An operation 1250 includes correcting the measured refraction of the subject's eye at the infrared wavelength with the customized chromatic adjustment factor to determine a refraction of the subject's eye at a visible wavelength in the visible spectrum.

In some embodiments, control and signal processing operations of method 1200 may be performed by one or more processors (e.g., processor(s) 61 of controller 60) of optical measurement system 1 in conjunction with associated memory (e.g., memory 62).

While certain illustrated embodiments of this disclosure have been shown and described in an exemplary form with a certain degree of particularity, those skilled in the art will understand that the embodiments are provided by way of example only, and that various variations can be made and remain within the concept without departing from the spirit or scope of the invention. Such variations would become clear to one of ordinary skill in the art after inspection of the specification, drawings and claims herein. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

We claim:

1. A method for measuring a characteristic of a subject's eye which includes a cornea and a lens, the method comprising:
    using a probe beam having an infrared wavelength in the infrared spectrum to measure a refraction of the subject's eye at the infrared wavelength;
    capturing at least two different Purkinje images at two different corresponding wavelengths from at least one surface of the lens of the subject's eye;
    determining from the at least two different Purkinje images a value for at least one parameter of the subject's eye;
    using the value of the at least one parameter to determine a customized chromatic adjustment factor for the subject's eye; and
    correcting the measured refraction of the subject's eye at the infrared wavelength with the customized chromatic adjustment factor to determine a refraction of the subject's eye at a visible wavelength in the visible spectrum.

2. The method of claim 1, wherein the at least two different Purkinje images include at least two Purkinje III images from an anterior surface of the lens.

3. The method of claim 2, further comprising measuring a curvature of the cornea of the subject's eye, wherein determining from at least two different Purkinje images a value for at least one parameter of the eye includes determining from the measured curvature of the cornea and the at least two Purkinje III images a change in an index of refraction of the cornea from the infrared wavelength to the visible wavelength.

4. The method of claim 3, wherein the at least two different Purkinje images further include at least two Purkinje IV images from a posterior surface of the lens.

5. The method of claim 4, wherein determining from at least two different Purkinje images a value for at least one parameter of the eye includes determining from the at least two Purkinje III images and the at least two Purkinje IV images a change in an index of refraction of the lens from the infrared wavelength to the visible wavelength.

6. The method of claim 4, wherein determining from the at least two different Purkinje images a value for at least one parameter of the eye includes determining from the at least two Purkinje IV images a radius of curvature of the posterior surface of a lens of the eye.

7. The method of claim 4, further comprising:
employing an optical coherence tomographer to measure a thickness of a lens of the eye; and
using the measured thickness of the lens to determine the customized chromatic adjustment factor for the eye.

8. The method of claim 2, wherein determining from the at least two different Purkinje images a value for at least one parameter of the eye includes determining from the at least two Purkinje III images a radius of curvature of the anterior surface of a lens of the eye.

9. The method of claim 1, wherein the two wavelengths include the infrared wavelength.

10. The method of claim 1, wherein the two wavelengths are both in the infrared spectrum.

11. The method of claim 1, wherein using the value for at least one parameter to determine a customized chromatic adjustment factor for the subject's eye includes performing ray tracing using an eye model including the at least one parameter, wherein the value for the at least parameter is employed in the ray tracing.

12. The method of claim 1, wherein using the value for at least one parameter to determine a customized chromatic adjustment factor for the subject's eye includes solving a linear equation wherein at least one variable in the linear equation corresponds to the at least one parameter, wherein solving the linear equation includes substituting the value for the at least one variable in the linear equation.

13. A system for making at least one objective measurement of a subject's eye, the system including:
an aberrometer comprising a light source configured to generate a probe beam having an infrared wavelength in the infrared spectrum, the aberrometer being configured to measure a refraction of the subject's eye at the infrared wavelength;
a light pattern generator configured to generate light patterns at two different wavelengths;
an image detector configured to capture at least two different Purkinje images at the two different wavelengths from at least one surface of the lens of the subject's eye; and
at least one processor, configured to:
determine from the at least two different Purkinje images a value for at least one parameter of the subject's eye,
determine a customized chromatic adjustment factor for the subject's eye based at least in part on the value of the at least one parameter, and
correct the measured refraction of the subject's eye at the infrared wavelength with the customized chromatic adjustment factor to determine a refraction of the subject's eye at a visible wavelength in the visible spectrum.

14. The system of claim 13, wherein the at least two different Purkinje images include at least two Purkinje III images from an anterior surface of the lens.

15. The system of claim 14, further comprising a corneal topographer configured to measure a curvature of the cornea of the subject's eye, wherein the processor is configured to determine from the measured curvature of the cornea and the at least two Purkinje III images a change in an index of refraction of the cornea from the infrared wavelength to the visible wavelength.

16. The system of claim 15, wherein the at least two different Purkinje images further include at least two Purkinje IV images from a posterior surface of the lens.

17. The system of claim 16, wherein the processor is configured to determine from the at least two Purkinje III images and the at least two Purkinje IV images a change in an index of refraction of the lens from the infrared wavelength to the visible wavelength.

18. The system of claim 16, wherein the processor is configured to determine from the at least two Purkinje IV images a radius of curvature of the posterior surface of a lens of the eye.

19. The system of claim 14, wherein the processor is configured to determine from the at least two Purkinje III images a radius of curvature of the anterior surface of a lens of the eye.

20. The system of claim 14, further comprising an optical coherence tomographer configured to measure a thickness of a lens of the eye, wherein the processor is further configured to determine the customized chromatic adjustment factor for the subject's eye at least In part using the measured thickness of the lens.

21. The system of claim 13, wherein the two wavelengths include the infrared wavelength.

22. The system of claim 13, wherein the two wavelengths are both in the infrared spectrum.

23. The system of claim 13, wherein the processor is configured to perform ray tracing using an eye model including the at least one parameter, wherein the value for the at least parameter is employed in the ray tracing.

24. The system of claim 13, wherein the processor is configured to solve a linear equation wherein at least one variable in the linear equation corresponds to the at least one parameter, wherein solving the linear equation includes substituting the value for the at least one variable in the linear equation.

* * * * *